(12) United States Patent
Spudich, Jr. et al.

(10) Patent No.: US 10,345,145 B2
(45) Date of Patent: Jul. 9, 2019

(54) MINIATURIZED SPECTROMETER FOR SENSITIVE AND ROBUST LABORATORY AND FIELD USE

(71) Applicant: Spectrum Perception LLC, St. Charles, MO (US)

(72) Inventors: Thomas A. Spudich, Jr., Lake Saint Louis, MO (US); Bradley L. Postier, St. Charles, MO (US); Jermey D. Weter, High Ridge, MO (US); Miranda Adams, Wentzville, MO (US); Ethan J. Vaughan, O'Fallon, MO (US)

(73) Assignee: SPECTURM PERCEPTION LLC, St. Charles, MO (US)

( * ) Notice: Subject to any disclaimer, the term of this patent is extended or adjusted under 35 U.S.C. 154(b) by 0 days.

(21) Appl. No.: 15/113,648

(22) PCT Filed: Jan. 23, 2015

(86) PCT No.: PCT/US2015/012787
§ 371 (c)(1),
(2) Date: Jul. 22, 2016

(87) PCT Pub. No.: WO2015/112919
PCT Pub. Date: Jul. 30, 2015

(65) Prior Publication Data
US 2017/0010154 A1 Jan. 12, 2017

Related U.S. Application Data

(60) Provisional application No. 61/930,684, filed on Jan. 23, 2014.

(51) Int. Cl.
*G01J 3/02* (2006.01)
*G01N 21/25* (2006.01)
*G01J 3/10* (2006.01)
*G01J 3/42* (2006.01)
*G01N 21/03* (2006.01)
(Continued)

(52) U.S. Cl.
CPC .......... *G01J 3/0256* (2013.01); *G01J 3/0264* (2013.01); *G01J 3/0272* (2013.01); *G01J 3/10* (2013.01);
(Continued)

(58) Field of Classification Search
CPC .... G01J 3/0256; G01J 3/42; G01J 3/10; G01J 3/0264; G01J 3/0272; G01N 21/251;
(Continued)

(56) References Cited

U.S. PATENT DOCUMENTS 3,200,650 A 8/1965 Morrill, Jr.
5,257,086 A 10/1993 Fateley et al.
(Continued)

FOREIGN PATENT DOCUMENTS

WO 2010027982 A2 3/2010
WO 2015112919 A2 7/2015

OTHER PUBLICATIONS

International Search Report, International Patent Application No. PCT/US2015/012787, dated Apr. 17, 2015, 14 pages.

*Primary Examiner* — Hwa Andrew Lee
(74) *Attorney, Agent, or Firm* — Lewis Rice LLC

(57) ABSTRACT

A miniaturized spectrometer capable of being held and carried in a person's hand and including all of the necessary elements for reliable quantification and characterization for laboratory purposes, of a variety of objects, including an analyte in solution, and that is also optionally adaptable for analysis of an analyte in gaseous phase, and/or on or imbedded in a solid surface.

30 Claims, 18 Drawing Sheets

(51) Int. Cl.
*G01N 21/51* (2006.01)
*G01N 21/64* (2006.01)

(52) U.S. Cl.
CPC .............. *G01J 3/42* (2013.01); *G01N 21/251* (2013.01); *G01N 21/51* (2013.01); *G01N 21/645* (2013.01); *G01N 2021/0346* (2013.01); *G01N 2021/6439* (2013.01); *G01N 2201/0221* (2013.01)

(58) Field of Classification Search
CPC ... G01N 2201/0221; G01N 2021/6439; G01N 21/645; G01N 21/51; G01N 2021/0346
See application file for complete search history.

(56) References Cited

U.S. PATENT DOCUMENTS

| | | |
|---|---|---|
| 5,917,592 A | 6/1999 | Skiffington |
| 6,013,528 A | 1/2000 | Jacobs et al. |
| 6,461,808 B1 | 10/2002 | Bodner et al. |
| 7,459,713 B2 | 12/2008 | Coates |
| 7,907,282 B2 | 3/2011 | Coates |
| 8,189,196 B2 | 5/2012 | Belz |
| 8,912,007 B2 | 12/2014 | Bjornson et al. |
| 8,940,523 B2 | 1/2015 | Follonier et al. |
| 2001/0055115 A1 | 12/2001 | Garver et al. |
| 2010/0034706 A1 | 2/2010 | Mathus et al. |
| 2010/0167412 A1 | 7/2010 | Xiao et al. |
| 2013/0095508 A1 | 4/2013 | Campitelli et al. |

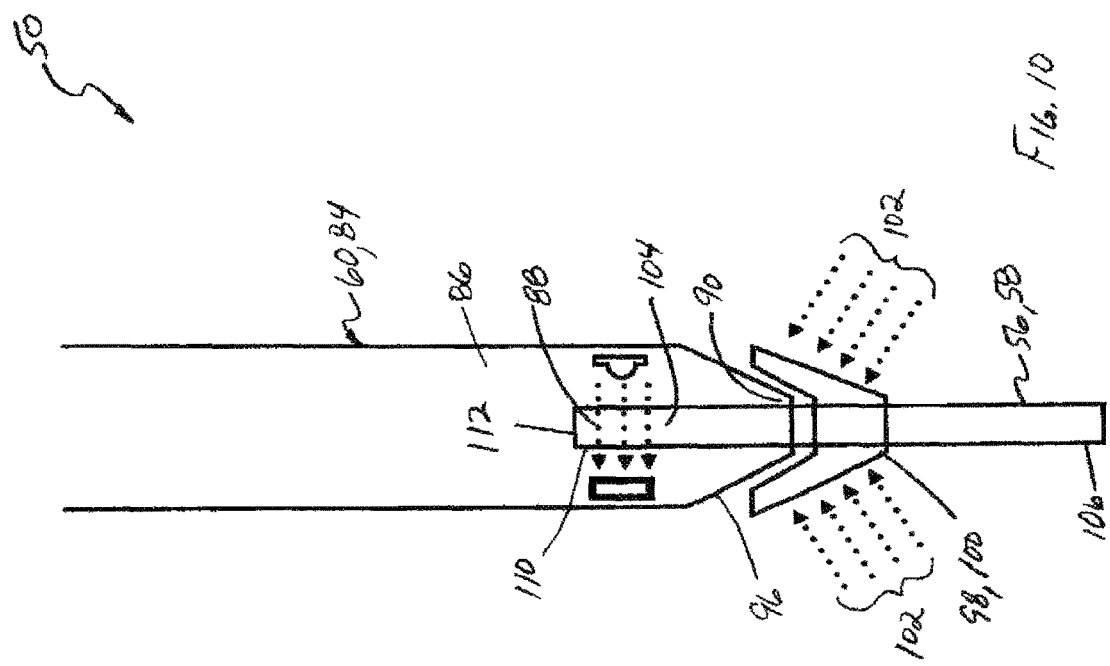

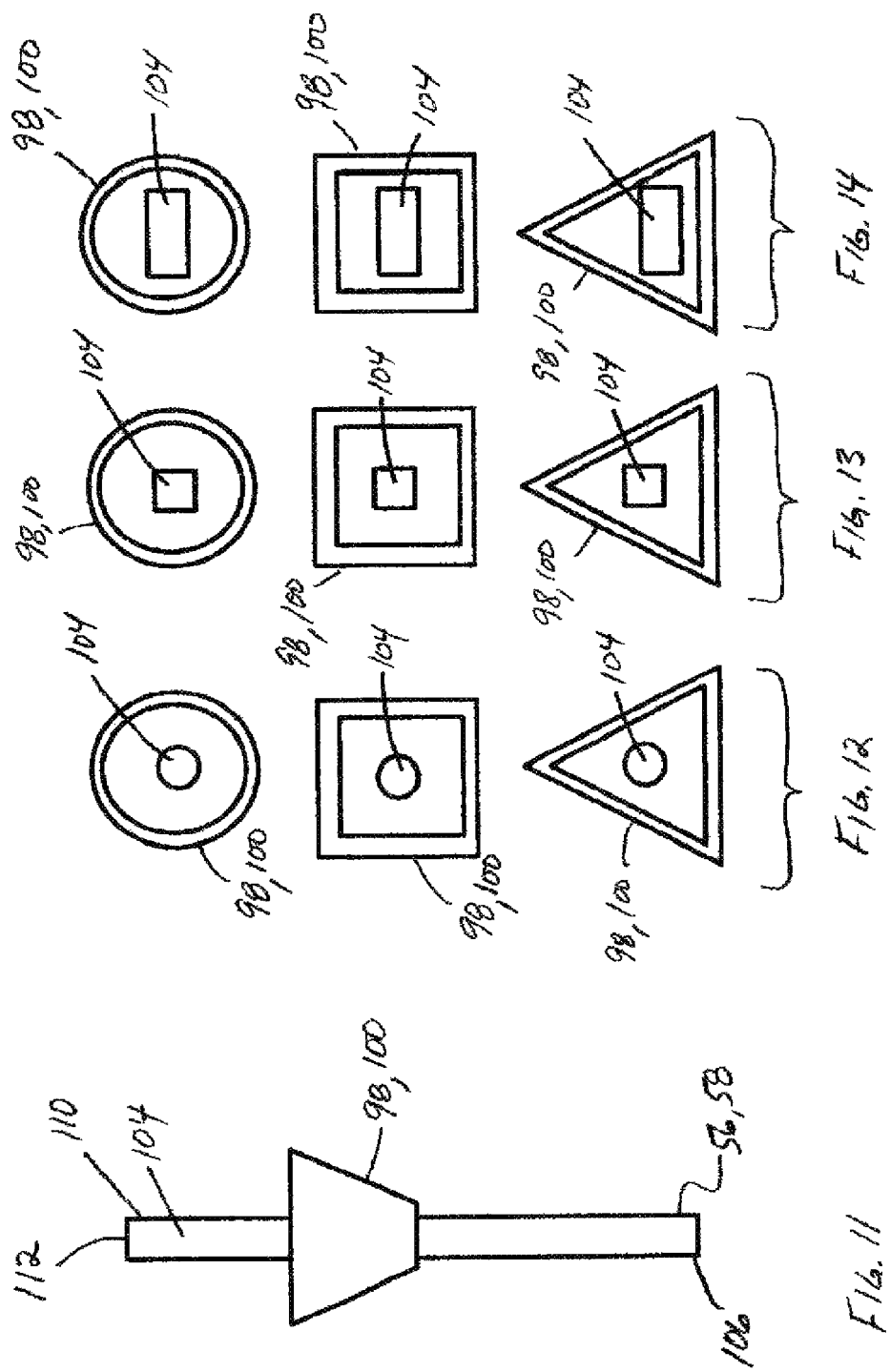

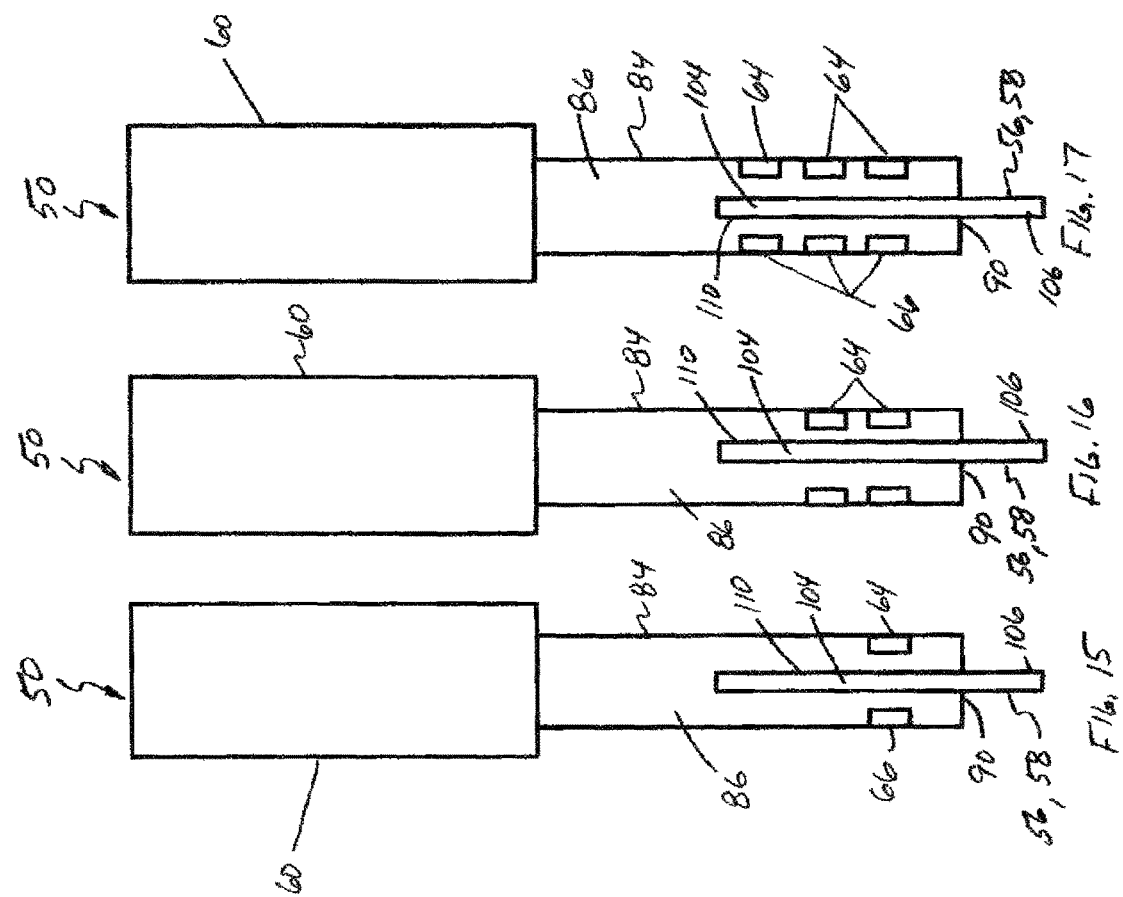

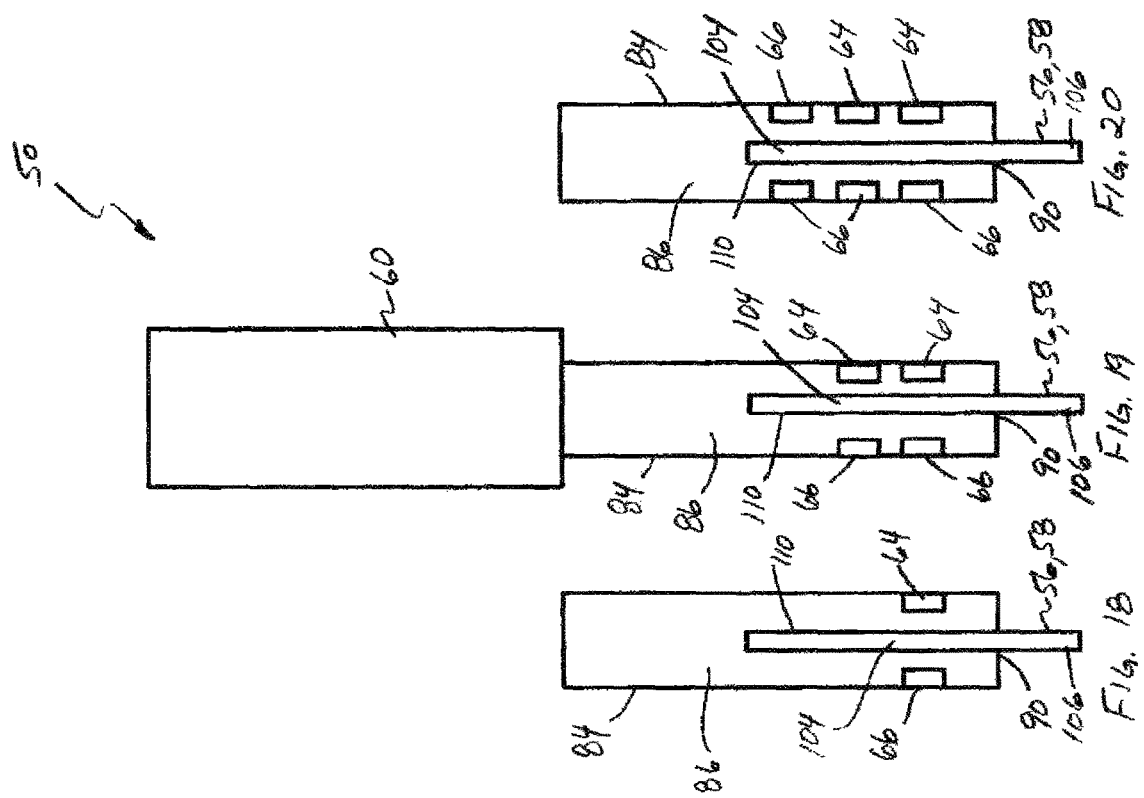

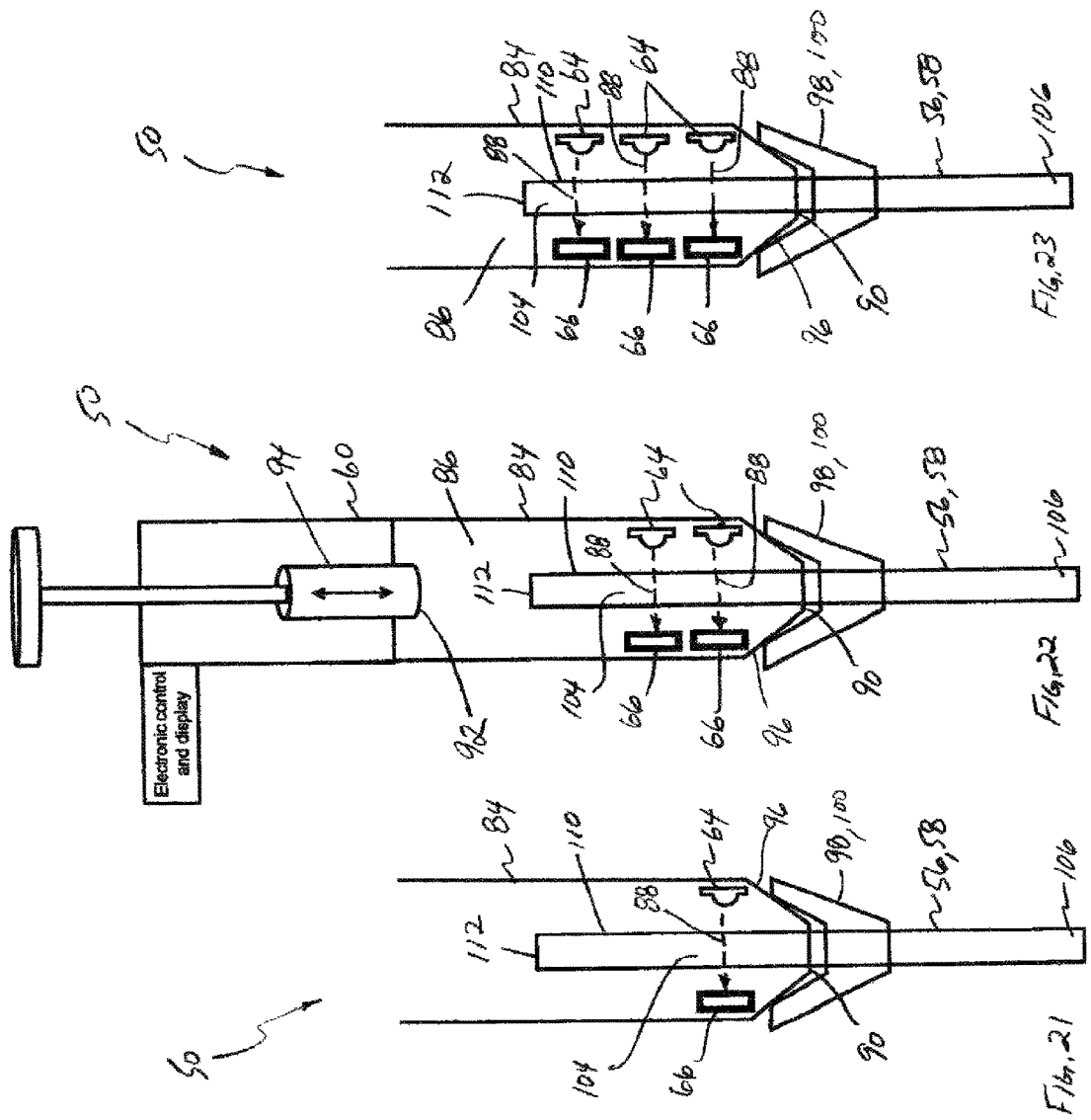

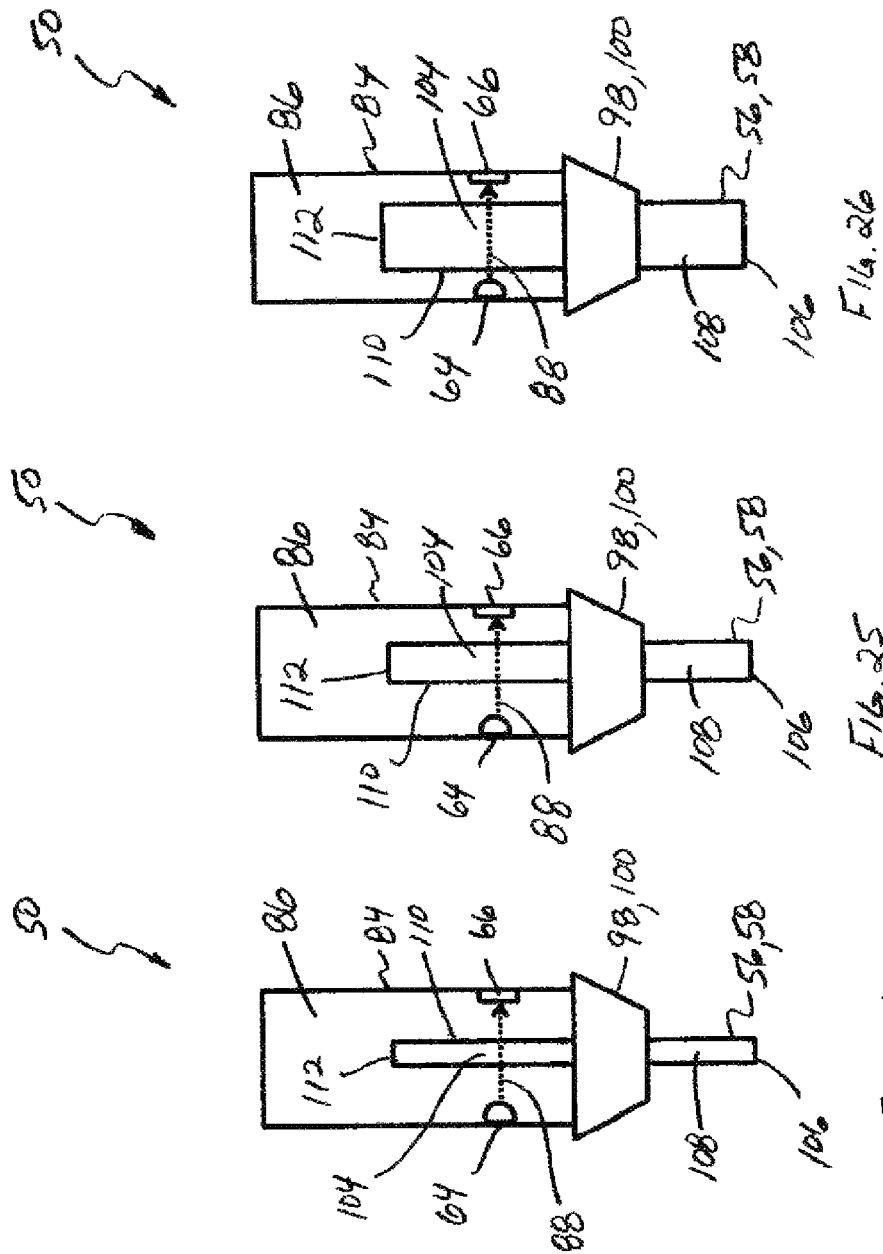

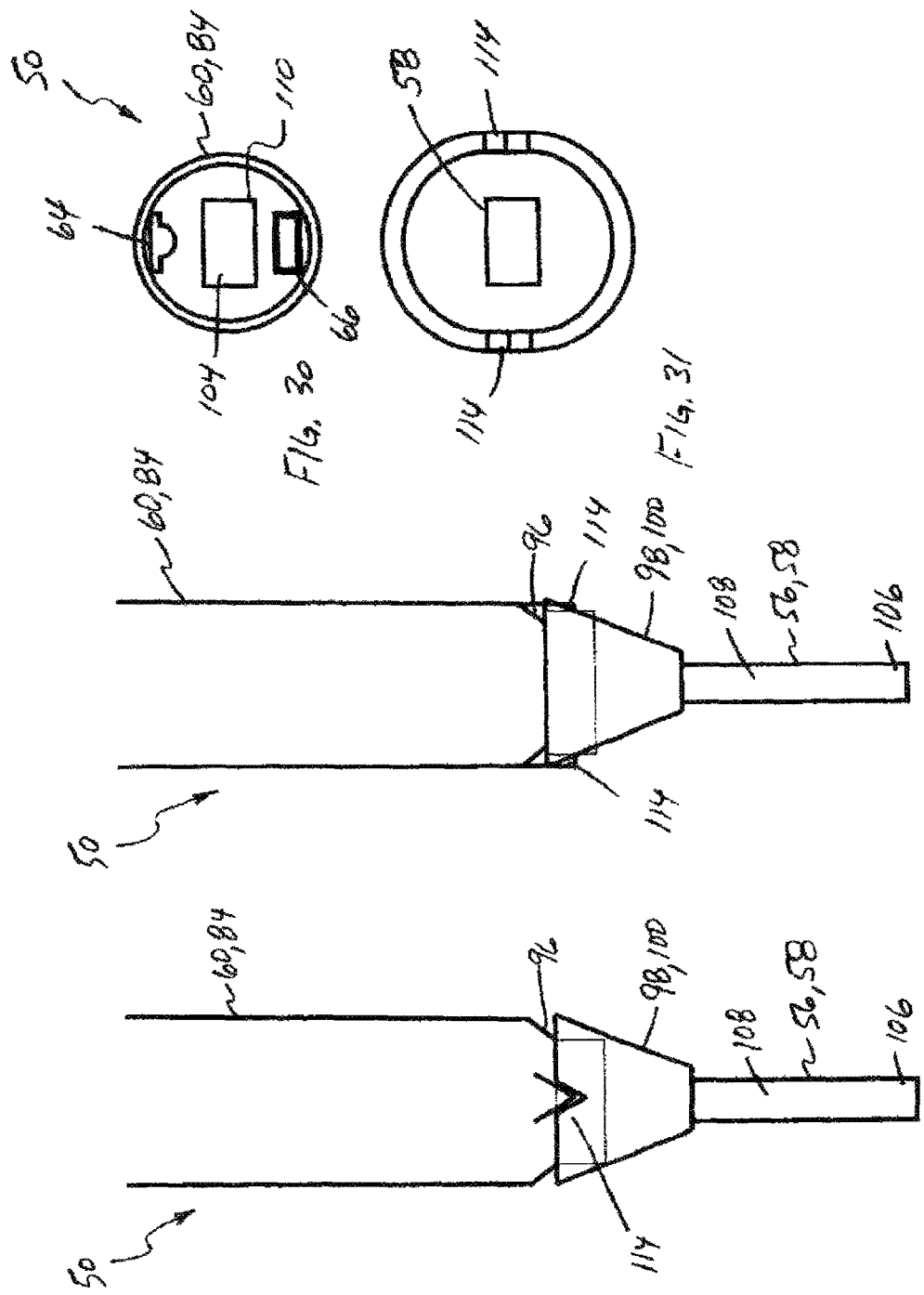

MINIATURIZED SPECTROMETER FOR SENSITIVE AND ROBUST LABORATORY AND FIELD USE

CROSS REFERENCE TO RELATED APPLICATIONS

This application is a § 317 U.S. National Phase of International Application Serial No.: PCT/US2015/012787 filed Jan. 23, 2015, which in turn claims the benefit of U.S. Provisional Application No. 61/930,684, filed Jan. 23, 2014. The entire disclosure of all the above documents is herein incorporated by reference.

TECHNICAL FIELD

The present invention relates generally to a miniaturized spectrometer capable of being held and carried in a person's hand and including all of the necessary elements for reliable quantification and characterization for laboratory purposes, of a variety of objects, including an analyte in solution, and that is also optionally adaptable for analysis of an analyte in gaseous phase, and/or on or imbedded in a solid surface.

BACKGROUND ART

U.S. Patent Application Ser. No. 61/930,684, filed Jan. 23, 2014, is incorporated herein by reference in its entirety.

Almost all forms of research require the detection and quantification of specific analytes to understand and/or characterize the phenomenon under study. Many types of methods have been applied to this detection ranging from the simple (gravimetric) to the technically complex (quantitative real-time RT-PCR and quantitative atomic force microscopy). The use of spectroscopic methods has come to be relied on heavily in analytical chemistry and the life sciences (Skoog & West, 1972). Analysis of the absorption, scattering, luminescence and fluorescence of light by a solute in solution (or a label on that solute) can enable the characterization of that solute. Spectrometers are utilized to measure the light or radiation altering properties of solutes or their surrogate analytes in solution for this purpose. Spectrophotometers or spectrometers can be multipurpose or designed and built for specific purposes. Multipurpose instruments have a common design mechanism described below while those with specific purpose may have alternative components and potentially simplified formats. Specific purpose instruments are less common but are advantageous for differing reasons including expense, size, data quality, environmental factors, mobility, ease of use, and sample concerns. Often the multipurpose instruments, while providing flexibility, have reduced sensitivity than when compared to the single purpose instruments which have been optimized for a single purpose.

Standard spectrophotometers require that the sample in question is placed in a cuvette directly in the path of a beam of light. The pathlength of standard cuvettes is 1 centimeter and thus typically requires significant volumes of sample for analysis. A sensor is placed in the light path downstream for detection of the light altering properties of the sample. The relationship of the light source, sample, and sensor is important for consistency of measured results. The light altering properties of the sample are typically compared against a reference sample (typically the same solvent without the target solute) to provide data regarding differences in light absorption, transmittance, scatter or emission. These differences are then associated with the solute of interest. Given a relatively pure solute with a known light absorption extinction coefficient, it is possible to determine the concentration and purity of that solute in solution using a spectrophotometer. There is a significant possibility for interference in more complex solutions or even due to the thermal energy supplied by the incident light beam. Spectrophotometers were originally using a single measuring beam (single-beam instrument) and correction for inferences was done by subtraction of a reagent blank as described above. To correct for temperature, light and other interferences a dual-beam approach was developed such that the sample with solute is run side by side with a sample without solute and subtracted in real-time to account for environmental and contaminant impacts. The whole science around spectrophotometric methods is very large and involves a highly versatile and powerful set of related techniques (Skoog & West, 1972).

Specialized spectrophotometers are designed with specific assays in mind. Some require smaller sample volumes (from 0.1 mL to nL), and new instruments have been developed that have eliminated the requirement of a cuvette (e.g., the NANODROP® from ThermoFisher for measuring nucleic acids). Other alternatives use specialized cuvettes that have reduced sample volume by the utilization of mirrored surfaces to redirect the light through alternative paths. Another modification to standard spectrophotometers is the ability to scan multi-well plates and arrays. This enables very high throughput, and standardized tests such as enzyme linked immunosorbent assays (Elisa) (Kennedy, Byrne, Fagain, & Berns, 1990; Lequin, 2005). Other examples include inline systems for analysis of products or cell densities for pharmaceutical and chemical reactors and blood monitors that clamp onto a patient's finger.

Some of the more common uses of spectrophotometers are for the determination of solute concentration in solution. For example, measuring the absorbance of light at 260 nm ($A_{260}$) can determine the concentration of nucleic acids in solution after extraction from biological samples (Grimsley & Pace, 2003; Powerwave, 2006; Sambrook & Russell, 2001; Willfinger, Mackey, & Chomczynski, 1997). Molecules such as protein, guanidinium salts, and phenol can increase the $A_{260}$ thus providing an inaccurate reading. These are common contaminants from nucleic acid preparations and need to be removed before accurate measurements of the extracted nucleic acids can be relied upon. These same compounds however absorb at other wavelengths. Specifically, protein has a peak absorbance at 260 nm while phenol and guanidinium salts absorb strongly at 230 nm. By comparing the absorption ratio at two wavelengths it is possible to determine the level of contamination by these compounds. Routinely, $A_{260:280}$ ratios are used to determine the level of protein contamination in a sample while $A_{260:230}$ ratios are used to determine the contamination due to either guanidinium salts or phenolic compounds. Further processing can reduce the contamination and this can be further confirmed by repeating the optical measurements. For these applications, the relationship of the light source, sample, and sensor must again be consistent amongst samples to be compared for enable obtaining reliable results.

Colorimetric assays are designed for indirect detection of a substance in solution. The target substance may be a chemical compound, enzyme, or unknown mixture of compounds. Colorimetric assays involve chemical or physical reactions that involve a substrate/enzyme or target/ligand of interest. The result of this chemical reaction is the production of a compound or complex that has altered light/radiation absorbing/emitting properties at a specific wavelength. Ideally the change in light properties is linear in response to the concentration of the specific substrate of interest within a useful range of substrate concentration. Some examples include the use of ferrozine to measure iron atoms, Coomassie blue for protein, and para-nitrophenyl-phosphate for phosphatase activity (Bradford, 1976; Grimsley & Pace, 2003; Martin, Pallen, Wang, & Graves, 1985; Stookey, 1970). Using a spectrofluorometer, it is also possible to detect the fluorescent emission of light from a fluorescent solute substrate or a fluorescently labeled solute for various purposes. Fluorescent spectroscopy can be linked to enzyme assays, studies of photosynthetic activity, cell enumeration, and various other fluorescence-based assays (Mason, 1993). Fluorescent probes and substrates have expanded the potential for sensitive detection of analytes of interest and generated a broad industry focused on its exploitation (Mason, 1993).

A specialized industry has developed about the use of luminescent assays which are at their core spectroscopy. However, in luminescent assays an enzyme/substrate pair are used to study analytes by generation of light within the sample and using the luminometer (the reading spectrometer) to record the light levels (Vdovenko et al, 2010). Advances in luminescent assays are even able to now produce multiple colors of light to allow multiplexed assays and more complexity within a specific sample to be studied. (Gilbert et al., 2011; Wesierska-Gadek, Gueorguieva, Ranftler, & Zerza-Schnitzhofer, 2005).

In general, as described above, spectrophotometers are large and complex instruments. These instruments are applicable in the chemical or biological laboratories for basic research, clinical diagnostics, biotechnology, chemical, and pharmaceutical industries, military applications, homeland security, and forensics laboratory setting. However, the instruments are too bulky to be mobile as they are often attached directly to a computer to drive the instrument and extract or analyze data. In general a focus on miniaturization has occurred but rather than decrease the instrument size (instrument miniaturization) the focus has been on decreasing sample size (assay miniaturization).

There is a real need for miniaturization of the spectroscopy instrument to reduce its overall cost and allow it to be more generally useful in the laboratory or the field. Ideally this would not come with a reduction in specificity or limit of detection (LOD) for the sample of interest. The single purpose NANODROP spectrophotometer has been able to bridge this gap, although is not easily portable and is a single analyte system.

Miniaturized spectrophotometers have been developed previously. However, they have met with little success and were not accepted broadly as a useful reliable instrument. An early device of Paul Hoogestater (US D237982, 1974) developed a battery operated single channel spectrophotometer for field use. This device presumably used an incandescent bulb and simple photosensor positioned on each side of the 1 cm cuvette sample port with an analog output for absorbance or transmittance. This may have been useful to measure samples like culture density and water sample clarity, but it would not have the accuracy necessary for molecular techniques to measure nucleic acid quality or abundance, nor would it work for fluorescence or luminescence. Several other miniature spectrometers have been pursued having applications with different targets and such do not incorporate many of the functional units described here in one instrument. For instance the spectrometer proposed by Ciaccia et al WO2000014496 A1 utilizes a PCM-CIA card attached to a laptop to drive an illumination source and detector. This instrument is tied directly to a computer and thus has less mobility and greater expense associated with the instrument. Jung et al (WO2003073457, 2003) describes an instrument utilizing LED illumination and photodiode detection in a device designed to analyze teeth surfaces. This device does not have a sample holder luminescence or fluorescence capability, or wireless connectivity, and is wired to a computer for data transfer and analysis. Such a device provides little mobility. A spectrometer developed by Crowley et al (WO1998022805) again isn't suitable for measurement of liquid samples in a sample port with defined light path as it demonstrates a probe that would be inserted into a patient's body for direct analysis of targeted tissues. Other known devices attempt to be broad spectrum spectrophotometers. Similarly Cheng-Hao et al (US20130308128) and Zhang et al (U.S. Pat. No. 8,345,226, 2013) have developed broad range spectrophotometers that are mobile, but do not serve the utility in a laboratory setting.

Therefore, what is sought is a portable and adaptable spectrometer with sufficient limits of detection to successfully compete with the more bulky and immobile laboratory grade devices, and which overcomes one or more of the limitations and shortcomings set forth above.

SUMMARY OF THE INVENTION

What is disclosed is a portable and adaptable spectrometer with sufficient limits of detection to successfully compete with the more bulky and immobile laboratory grade devices, and which overcomes one or more of the limitations and shortcomings set forth above.

According to a preferred aspect of the invention, the miniaturized spectrometer is embodied in a structure having a sufficiently small overall size and mass to be carried by a hand from place to place and includes an enclosure defining and defining an internal cavity and an opening connected thereto, and mounting structure disposed about or adjacent to the opening operable to releasably hold a tubular sample holder so as to extend outwardly therefrom in at least substantially sealed connection therewith to allow transfer of a gas between an open end of the sample holder and the internal cavity. The miniaturized spectrometer includes at least one light source disposed and operable to emit a light beam along a light path within the internal cavity in predetermined relation to the mounting structure, and at least one light detector disposed along the light path to receive the light beam, or to receive a portion of the light beam reflected by an object in the light path, or to receive a light emission from the object, and to output at least one signal representative thereof. The miniaturized spectrometer additionally includes a processor connected to the light detector or detectors for receiving the signal outputted thereby, respectively, and is programmed to automatically process the at least one signal to determine at least one characteristic of an object in the light path.

As attendant advantages of the invention, the spectrometer can serve as a handheld, mobile, single-purpose spectrophotometer, or as a modular multipurpose spectrophotometer, both embodiments being capable in many instances to non-destructively measure analytes in very small sample volumes with little or no loss of sample if desired. The handheld device is miniaturized, yet has all necessary onboard elements to collect sensor outputs, process them to provide readable analyte characteristic data.

As additional preferred aspects of the invention, the miniaturized spectrometer can include desired input, memory, display, and output devices. Suitable input devices can include a touch screen, switch, and/or switch array, usable for selecting from amongst programmed options and inputting commands. Suitable display and output devices can include the touch screen or other direct user visible device, and communications apparatus for connection to a computer, tablet, smartphone, or other electronic device for downloading the data thereto, in a suitable manner, e.g., wired or wireless communications connection, for further analysis and recording. The onboard memory device can be permanent or removable, e.g., micro SD card, etc., and configured so that data can be stored on the device for later downloading/recording. This is advantageous as it allows measurements at the sampling location reducing the need to collect samples, and allows analysis of the stored data at a laboratory at another location. The system is robust so it can be used on the production line, lab bench, patient bedside, or in the field.

As an optional aspect of the invention, all or some of the above processor driven components of the spectrometer can be provided by a smartphone, tablet or other commercially available programmable microprocessor based device carried on or with and integrated with the other components of the miniaturized spectrometer.

As an example of the utility of the invention, for analysis of a particular known analyte, the light source can comprise a light emitting diode or diodes operable to produce a light beam having a narrow emission spectrum and peak emission near the maximum absorbance of the analyte. The sample holder can comprise a capillary tube of fixed internal diameter situated along the light emission path, and a suitable light sensor, e.g., a photodiode detector in the light path or shadow of the sample configured to convert the detected light intensity to a DC voltage. The microprocessor within the device will then process the DC voltage signal output, such as, but not limited to, to determine an average voltage output and use it to compute an average absorbance value. This can then be displayed and/or transmitted to a computer, tablet, or smartphone for further analysis in a suitable manner, e.g., via wired or wireless connection; and/or displayed on the touch screen or other display device of the spectrometer for manual recording, etc., before or after analysis by any external computer interfaced with the device.

According to another optional aspect of the invention, the spectrometer can be configured as a spectrofluorometer, essentially by locating the detector device or devices beside the light path so as to detect indirect light emissions from the sample, including prior to, during, and/or after illumination by the light source or sources, and the microprocessor can be programmed to execute the analysis in the desired manner.

Representative examples of possible light sources for use in the invention, can include, but are not limited to, deuterium, tungsten, xenon, or mercury incandescent lamps, or a light emitting diode or diodes of narrow or broad emission spectrum. As non-limiting representative examples, the light detector can comprise one or more photodiodes, CMOS, or CCD detectors, configured to absorb light within a designated narrow or broad spectrum, and may absorb light within the ultraviolet, visible, or infrared range. The limited bandwidth capabilities of the light source(s) and/or detector(s) can be an intrinsic feature, or achieved using appropriate light filtering in the well-known manner.

As an optional configuration of the invention, the light source can comprise one or more fiber optic components (e.g., wires or cables) that direct the light from the light source to the sample, and/or from the sample to the detector or detectors. These fiber optic may also be split such that two separate beams of light are produced such that one passes through the sample of interest and the other is used as a reference beam, such dual beam correction or calibration for or could correct for outside influences on the reading, e.g., ambient or environmental light intrusion.

According to another optional aspect of the invention, the spectrometer can be configured to be modular, wherein one section or component includes the input, output/display, processor, and another section or component includes the light source, sample holder, photodetector, and any attached fiber optic cables/wires. The power source can be still another component, e.g., detachable battery, or incorporated into one of the other components. As another option, the spectrometer can be configured to use different light sources, detectors, and sample holders, to facilitate analyzing different samples and/or analysis. As non-limiting examples in this regard, one optional light source can be configured to include a single emitter that emits a single narrow band of light or a broad spectrum. Another can be configured to include different/multiple emitters that emit a different bandwidth or bandwidths. Both can be configured to emit over different or multiple light paths, as desired or required for analysis of a particular analyte.

As still another optional embodiment, the enclosure and mounting structure and associated light source(s) and/or detector(s) can be configured or configurable or adaptable for holding different size samples, e.g., a 1 mm capillary; or a standard 1 cm cuvette, either having a variety of shapes, such as, but not limited to, rectangular, triangular, round, or oval shape, or the component can be configured with no solid support at all or a removable support.

As another optional embodiment of the present invention, the onboard power source can comprise one or multiple standard or rechargeable batteries to power the light source, the microprocessor, input, display, and output devices, and any other onboard electrified component as necessary.

Another optional embodiment of the present invention includes one or several options for wireless connectivity including a desktop computer, laptop computer, tablet computer, handheld smartphone, or any device for collecting analyzing, and displaying data.

Another optional embodiment of the present invention includes a computer code to control the status and intensity of the light source through means of current or voltage, and can be selectable using the input device or preprogrammed.

Another optional embodiment of the present invention includes a computer code to collect and convert voltages applied by the photodiode into light intensity values along with comparison of the target samples and reference samples to determine light absorbance, scattering, or fluorescence by the sample.

Another optional embodiment of the present invention includes an input device, e.g., touch screen display, switch, or button, on the surface of the spectrometer and connected to the microprocessor to input selections or commands that will allow the selection of type of analyte to be tested and/or to designate that a certain sample is to be used as a reference.

In another optional aspect of the invention, the device measures the fluorescent reemission of light by the analyte at a longer wavelength than that of the emission of the light source.

In another aspect of the invention, the spectrometer is attached to a handheld device such as a smartphone or tablet such that the smartphone will utilize internal software to drive the spectrophotometer, as well as collect, present, and record data, thus providing all or some of the required processing.

As still another optional aspect of the invention, a sample holder for attachment to the miniaturized spectrometer is provided, having a cavity through which a light beam will pass, comprising: a mounting element engageable with a mounting structure on the spectrometer for releasably holding the mounting element in a predetermined position on spectrometer; a tubular sampling tip extending in a predetermined first direction from the mounting element and having an interior passage open at opposite ends; and a tubular sample holder extending in a predetermined second direction from the mounting element, the sample holder including an interior cavity bounded by light transmissive surfaces to allow passage of a light beam therethrough and having an opening connected to one of the ends of the interior passage of the tubular sampling tip to allow passage of a fluid therebetween, and another opening to allow introduction of a negative pressure condition into the interior cavity.

BRIEF DESCRIPTION OF THE DRAWINGS

A better understanding of the exemplary embodiments of the invention will be had when reference is made to the accompanying drawings, and wherein:

FIG. 10 is a simplified sectional view all aspects of an embodiment of a miniaturized spectrometer of the invention, illustrating the light blocking properties of a sample holder thereof.

FIG. 11 is a simplified side view of one embodiment of a sample holder for use with the spectrometer of the invention.

FIG. 12 shows end views of a round sample holder with alternative round, rectangular, and triangular mounting elements for releasably mounting on a spectrometer of the invention.

FIG. 13 shows end views of a rectangular sample holder with alternative round, rectangular, and triangular mounting elements for releasably mounting on a spectrometer of the invention.

FIG. 14 shows end views of a triangular sample holder with alternative round, rectangular, and triangular mounting elements for releasably mounting on a spectrometer of the invention.

FIG. 15 is a simplified side view of a spectrometer of the invention showing one embodiment of a light source and light detector combination of the invention.

FIG. 16 is a simplified side view of a spectrometer of the invention showing another embodiment of a light source and light detector combination of the invention.

FIG. 17 is a simplified side view of a spectrometer of the invention showing another embodiment of a light source and light detector combination of the invention.

FIG. 18 is a simplified side view of a spectrometer of the invention showing a replaceable barrel including a one embodiment of a light source and light detector combination of the invention, illustrating a modular capability.

FIG. 19 is a simplified side view of a spectrometer of the invention showing a replaceable barrel including another embodiment of a light source and light detector combination of the invention, illustrating another modular configuration.

FIG. 20 is a simplified side view of a spectrometer of the invention showing a replaceable barrel including another embodiment of a light source and light detector combination of the invention, illustrating the modular capability.

FIG. 21 is a simplified side view of a spectrometer of the invention, including a single light source/detector combination, showing representative mounting apparatus for mounting a sample holder in predetermined relation to the combination.

FIG. 22 is a simplified side view of a spectrometer of the invention, including a two light source/detector combination, showing representative apparatus for mounting a sample holder in predetermined relation thereon.

FIG. 23 is a simplified side view of a spectrometer of the invention, showing representative apparatus for mounting a sample holder in predetermined relation thereon.

FIG. 24 is a simplified side view of a barrel of a spectrometer of the invention, showing one embodiment of a sample holder mounted thereon in predetermined relation to the light source/detector combination.

FIG. 25 is a simplified side view of a barrel of a spectrometer of the invention, showing an embodiment of a wider sample holder mounted thereon in predetermined relation to the light source/detector combination.

FIG. 26 is a simplified side view of a barrel of a spectrometer of the invention, showing an embodiment of a still wider sample holder mounted thereon in predetermined relation to the light source/detector combination.

FIG. 28 is a simplified side view of a barrel of a spectrometer of the invention, showing an embodiment of apparatus for aligning a sample holder therewith.

FIG. 29 is a simplified side view of a barrel of a spectrometer of the invention, showing another embodiment of apparatus for aligning a sample holder therewith.

FIG. 30 is an end view of a barrel of a spectrometer of the invention.

FIG. 31 is an end view of a sample holder having an alternative oval shape mounting element incorporating aligning apparatus for mounting on a spectrometer of the invention.

DETAILED DESCRIPTION OF THE INVENTION

Using a variety of compositions, exemplary embodiments of a spectrometer 50, 52, and 54, also referred to a spectrophotometer, of the invention are directed at improving the miniaturization and therefore mobility and utility of spectrophotometers.

Figure 1:
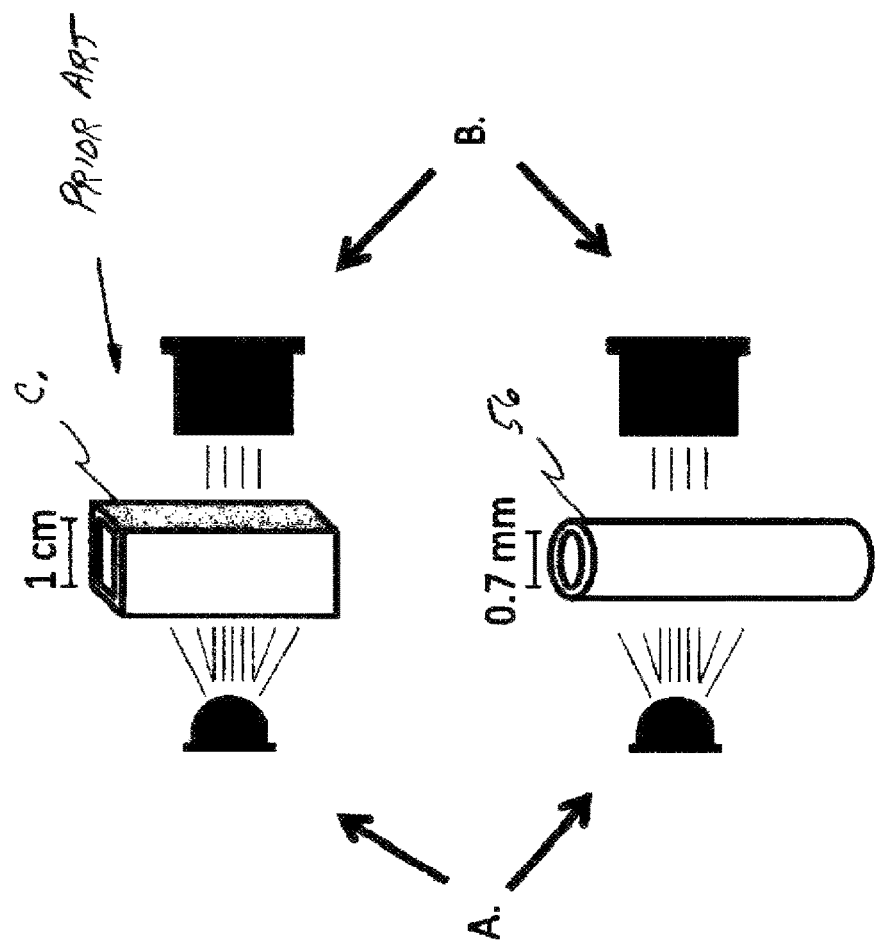
FIG. 1 is a representative arrangement of a light source and light detector in relation to the alignment of a standard cuvette shown above and a capillary cuvette shown in the bottom image. Transmitted light detected by the sensor is converted to Absorbance, optical density, fluorescence, or light scattering.

Basic elements of spectrophotometry are illustrated in FIG. 1 and include a light source or sources, denoted generally by the letter "A"; and a light detector or detectors, denoted generally by the letter "B". A sample holder, conventionally in the form of a rectangular cuvette, denoted by the letter "C", or a round cuvette, denoted by the letter "D", containing a sample of a substance or analyte is placed in a light path between source(s) A and detector(s) B. An outputted signal of the detector(s) B which will be representative of light received, is processed to determine presence, quantity, and/or a property or characteristic of the analyte, as discussed under the Background of the Art heading above. Sectional size of the cuvette (whether rectangular or round) will typically be about 1 cm, which is standard, as denoted by the curette C, although it should be noted that other sectional sizes are known. For miniaturization according to the invention, a much smaller sectional extent is sought, on the order of about 1 mm overall and about 0.7 mm internal sectional extent, as illustrated by the sample holder 56, when suitable and permissible for a particular substance or analyte to be analyzed.

Figure 2:
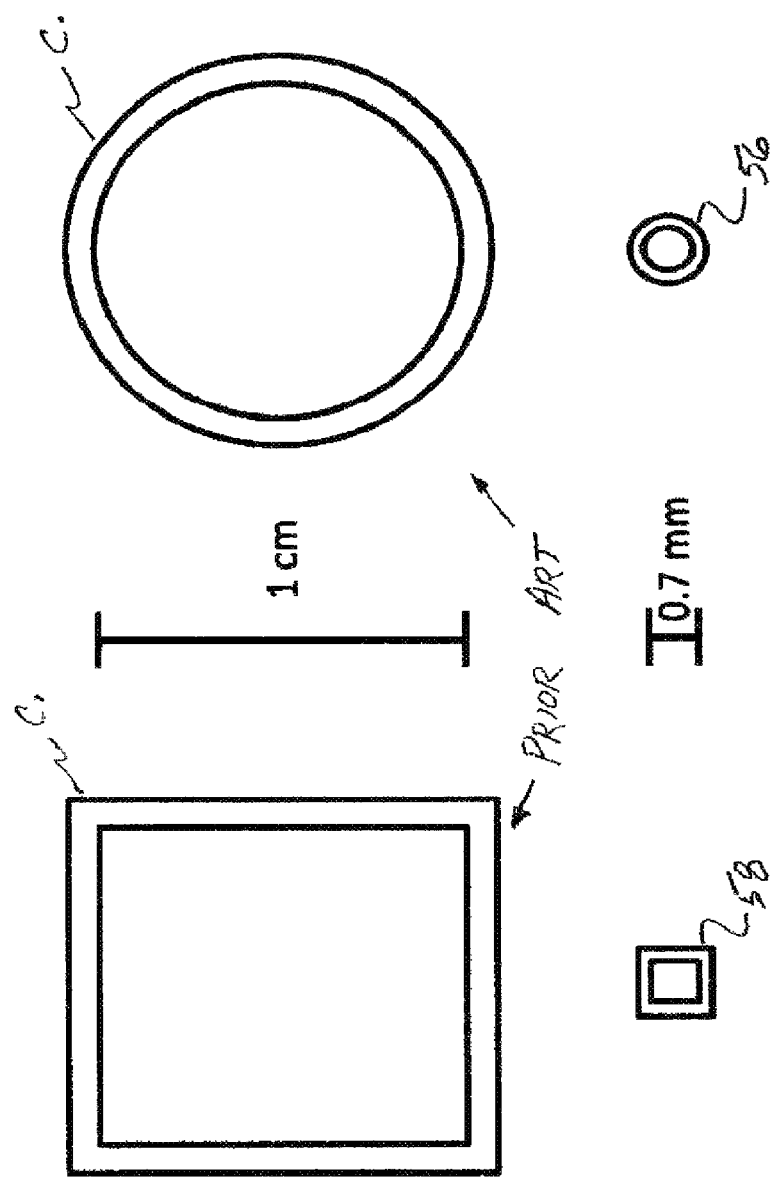
FIG. 2 show exemplary embodiments of optical cross sections of a standard rectangular cuvette, a round cuvette of the same inner sectional extent, and smaller cuvettes to reduce sample volume requirements.

FIG. 2 illustrates the volumetric difference between standard 1 cm extent rectangular and round curettes C., and smaller sample holders 56 (round) and (rectangular) sought to be used with the invention (note illustrations not to scale).

Figure 3:
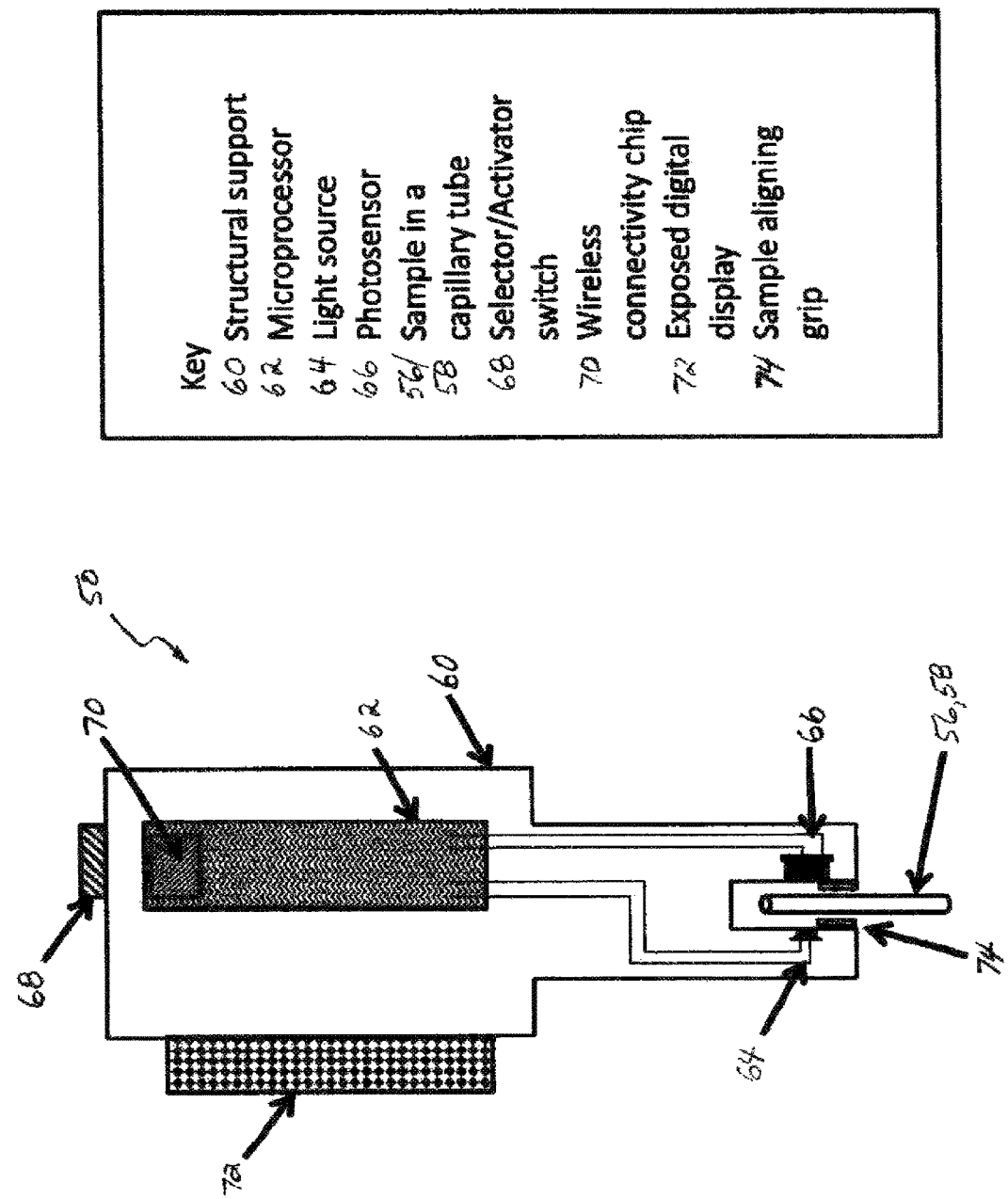
FIG. 3 is an illustration of a general arrangement of components of one embodiment of a miniaturized spectrophotometer according to the invention, accompanied by a product key identifying the components.

FIG. 3 shows one embodiment of a miniaturized spectrometer 50 constructed and operable according to the invention. Components of spectrometer 50 include a structural support in the form of a body 60 having a sufficiently small overall size and mass to be carried by a hand from place to place. Body 60 supports a processor 62, here a suitable commercially available microprocessor; a light source 64, here one or more commercially available LEDs; a light detector 66 which here is a commercially available photosensor device, a sample holder 56 or 58; an input device 68 which here is a selector/activator switch; an output device, here, a commercially available wireless connectivity chip; a display device 72, such as a commercially available digital LCD or LED display; and sample support or mounting structure 74, here a sample aligning grip, for holding an analyte sample or sample holder in a light path of light source 64 and in desired relation to light detector 66.

Figure 6:
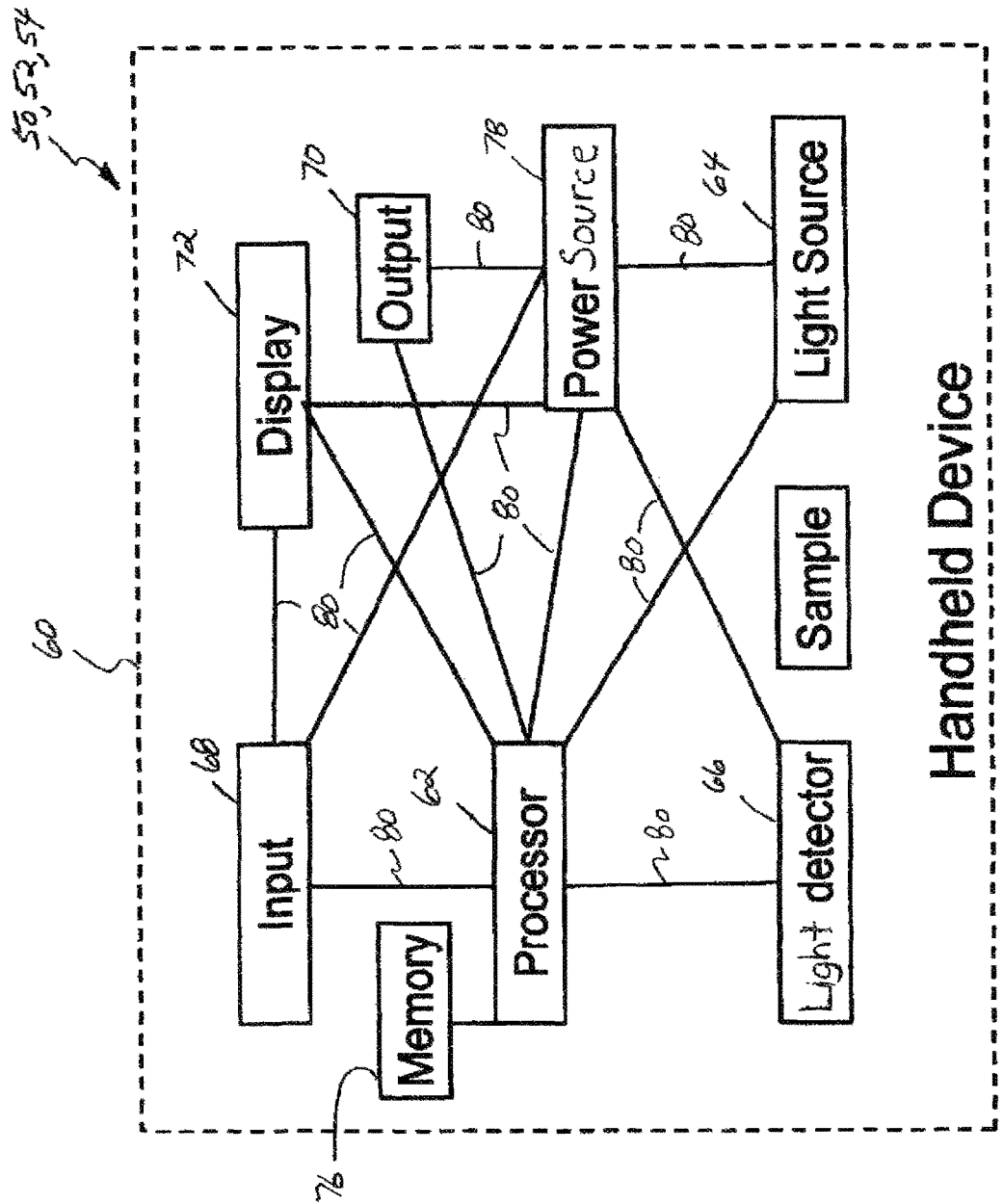
FIG. 6 is a diagram illustrating elements of a miniaturized spectrometer of the invention.

FIG. 6 is a simplified schematic diagrammatic representation showing a preferred system architecture including preferred components and their connections, for a miniaturized spectrometer such as spectrometers 50, 52, and 54, constructed and operable according to the invention. Components include the structural support 60, which will be body, e.g., injection molded plastics, metal, or a combination, compact and light enough to be carried by a person in his or her hand yet robust enough for field use; processor 62, which will be a suitable microprocessor programmable and operable for executing required routines and computations such as would drive a commercially available smart phone, PDA, or tablet; an associated memory 76, which can be permanent and/or removable, e.g., micro SD card format; light source or sources 64, e.g., one or more LEDs; light detector or detectors 66, e.g., one or more photosensors or photodiodes; a power source 78, such as a suitable commercially available battery for handheld electronics; an input device 68; a display device 72, which can be separate or combined, e.g., touchscreen; and output device 70, e.g., USB or Bluetooth, LAN radio. The components are connected by suitable conductive paths 80 in their conventional manner, e.g., which can comprise wires of a wiring harness or network, and wireless connections where appropriate.

Figure 7:
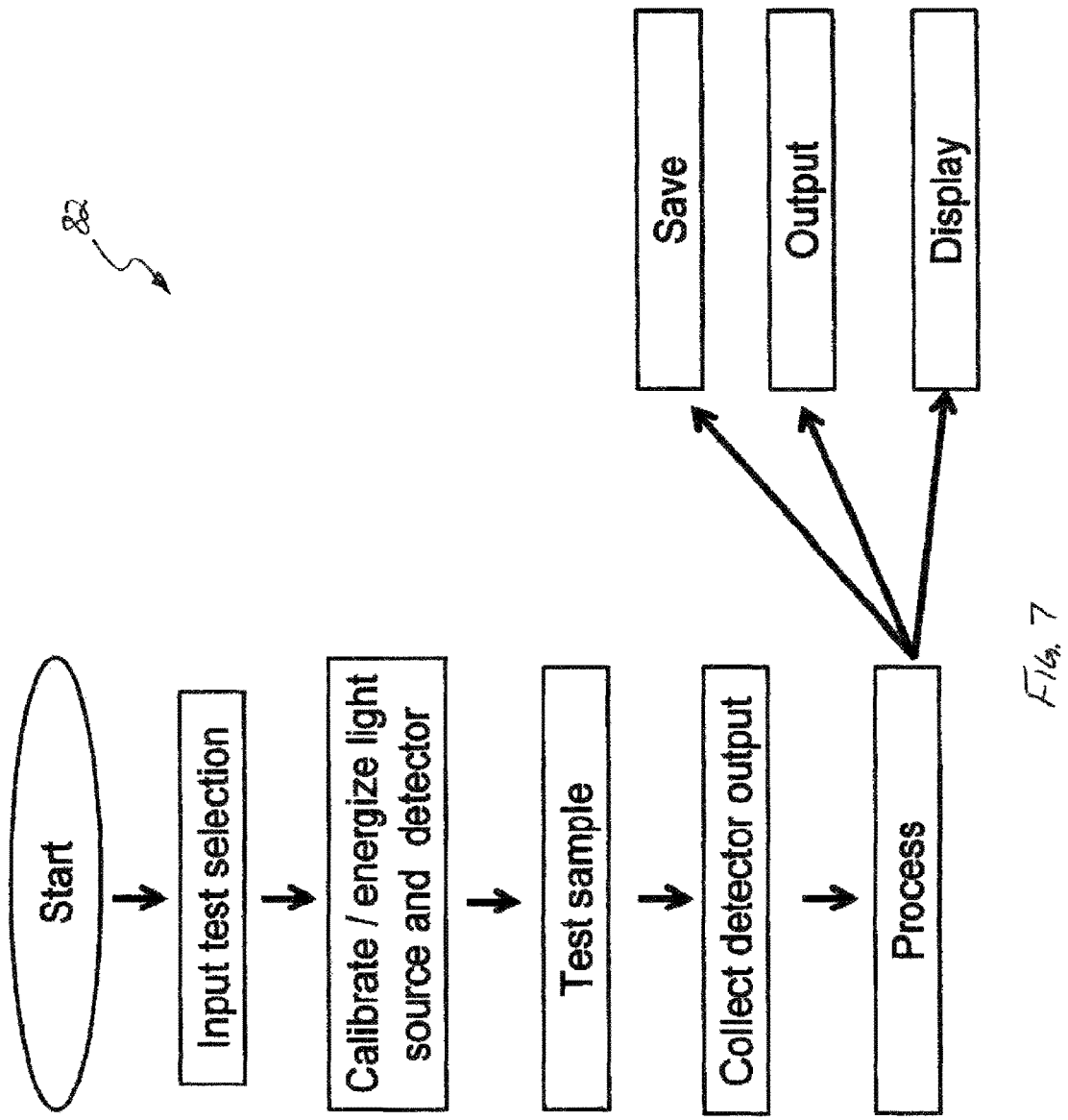
FIG. 7 is a simplified flow diagram showing steps of operation of a miniaturized spectrometer of the invention.
Figure 8:
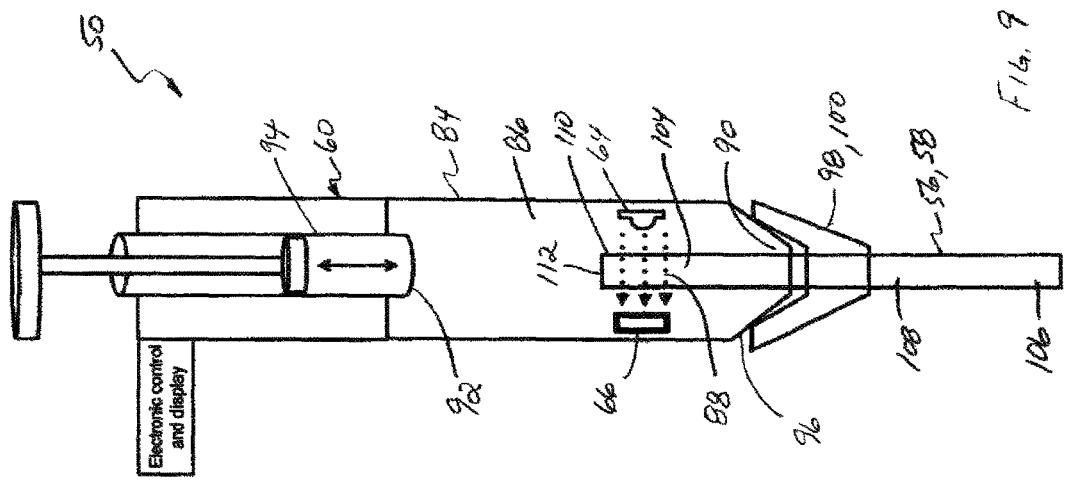
FIG. 8 is a simplified sectional side view of an embodiment of a miniaturized spectrometer of the invention.
Figure 9:
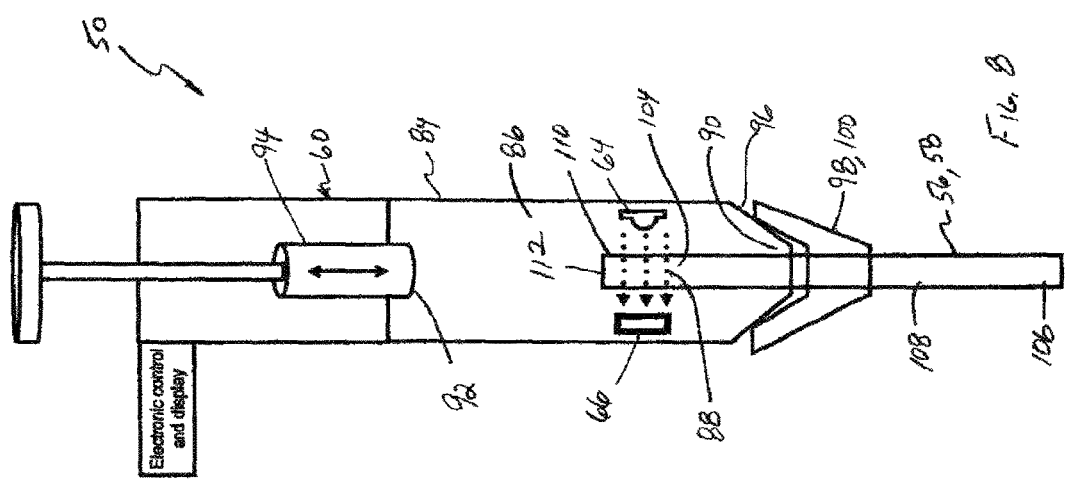
FIG. 9 is a simplified sectional side view of another embodiment of a miniaturized spectrometer of the invention.

A flow diagram showing basic operating steps of a spectrometer 50, 52, 54 is shown in FIG. 7. Essentially, operation is commenced by a user by turning on the device. As the preferred step, the processor will be programmed to display one or more options, such as a broad light spectrum; narrow spectrum; selectable individual wavelength or wavelengths; or a predetermined analyte, or the like. As a next preferred step, the processor will be programmed to automatically calibrate and energize the light source and light detector, which may entail use of a calibrating sample or clean solution. The analyte sample to be tested or analyzed is then inserted or loaded, e.g., mounted in a sample holding enclosure of the spectrometer automatically by the spectrometer, as controlled by the processor. Output signal data from the light detector or detectors is then received and processed by the processor, e.g., calculating a light absorption value as a function of an output voltage value. The calculated data is then saved, outputted, and/or displayed.

FIGS. 8-35 illustrate various contemplated embodiments of miniaturized spectrometers 50, 52, 54, according to the invention, as well as preferred sample holders and mounting arrangements. Here, it is contemplated to be advantageous for the miniaturized spectrometers of the invention to have a basic size of a commonly used laboratory handheld pipette used for drawing a sample analyte from a container and transferring it to a curette for spectroscopy and other purposes.

Structural support 60 in the form of a handheld body will include an enclosure 84 defining and bounding an internal cavity 86 that houses light source or sources 64 and light detector or detectors 66 in predetermined relation so that the light detector(s) 66 is/are disposed along a light path 88 of light emission of a specified light source or sources 64, as well as the sample holder 56, 58 in desired relation thereto. Enclosure 84 is preferably in the form of a barrel, having a first opening 90 through which the sample or sample holder, e.g., sample holder 56 or 58, is received, and a second opening 92 through which a negative pressure or partial vacuum is introduced into cavity 86 and the interior of the associated sample holder, as will be explained. The partial vacuum condition is produced using appropriate partial vacuum producing apparatus 94, here illustrated as a manually operated syringe, but which can alternatively comprise a vacuum pump or other device operable to evacuate cavity 86 to a required extent. Apparatus 94 is preferably incorporated into and carried on structural support 60, but can comprise a line or tether connected to a vacuum source such as a laboratory vacuum system.

Structural support 60 and/or enclosure 84 preferably includes mounting structure 96 configured to releasably mount a sample holder thereon in predetermined relation to the light path or paths 88 of light source or sources 64. In a preferred embodiment, mounting structure 96 is an external frusto-conical shape surface on enclosure 84 disposed about first opening 90. The sample holders to be used with the particular spectrometer will have a corresponding mounting element 98 having a mating internal frusto-conical shaped surface disposed thereabout so as to be releasably matingly engageable therewith in predetermined relation to the light source or sources 64. This predetermined relationship essentially positions a predetermined portion of the sample holder 56, 58 within internal cavity 86, in the light path or paths 88. Engagement of mounting element 98 with mounting structure 96 essentially comprises a manually applied or frictional fit therebetween sufficient to hold the sample holder and achieve and maintain the partial vacuum condition within internal cavity 86 during the analysis. This preferred manner of attachment is essentially that used for attaching sampling tips to laboratory pipettes, except that the sample holder intentionally extends into cavity 86 so as to be located in the light path or paths 88.

As an additional preferred feature for at least when analyzing light sensitive or photo reactive substances, mounting element 98 is incorporated into an annular collar 100 having light blocking or opaque properties, either full or to a desired extent. As a non-limiting example, collar 100 can be composed of an opaque plastics material, or have a coating or covering such as a paint or dye on its outer and/or inner surface. This in combination with the frictional fit provides an essentially complete block to passage of light 102 (see FIG. 10) about the sample holder. As exemplified by the round, rectangular, and triangular shapes in FIGS. 12, 13, and 14, mounting element 98 and collar 100 can have about any desired shape (suitable for mating with mounting structure 96) including other polygonal and rounded shapes, and can be used with sample holders of various shapes, including but not limited to round, rectangular, triangular (shown) as well as oval and other polygonal shapes. Other suitable mounting structure/mounting element arrangements can include, but are not limited to, threaded or barbed fasteners, mechanical detents, magnetic fasteners, spring loaded twist and lock fasteners, and the like.

It is contemplated that it may be desired to provide a modular construction spectrometer for various reasons, including such as to allow cleaning and disinfecting of components that contact samples or other potential contaminants, and to allow interchanging light components, e.g., one, two, three, or more light sources 64 and/or light detectors 66, or use with different type or size sample holders, as illustrated by FIGS. 15-26. In this regard, examining FIGS. 15, 16, and 17, it is contemplated that the spectrometer can have different interchangeable structural supports 60 and attached enclosures 84 having different arrangements of light sources 64 and light detectors 66, with or without mounting structure 96. In this regard, it is contemplated that for some applications the sample holders can be inserted into cavity 86 without the need of substantial mounting apparatus and an aligning grip or the like may be sufficient. Referring to FIGS. 18, 19, and 20, it is illustrated that alternatively, different enclosures 84 can be modularly connected to or mounted on the structural support 60, and can include various or the same light emitting apparatus as desired or required for a particular analysis. FIGS. 24, 25, and 26 illustrate that the enclosure and light emitting apparatus can be configured to accommodate sample holders of different sectional extents, e.g., 1 mm, 10 mm, and larger.

In each of the illustrated embodiments, it can be observed that the sample holders 56 and 58 extend into internal chamber 86 sufficiently to locate the subject analyte in the associated light path or paths 88. To achieve this, sample holders 56, 58 each have a cavity in a predetermined location through which a light beam will pass. In a preferred construction, the sample holders 56, 58 additionally includes a tubular sampling tip extending in a predetermined first direction from mounting element 98 and having an interior passage 108 open at opposite ends; and a tubular sample holding portion 110 extending in a predetermined second direction from mounting element 98 and including or incorporating interior cavity 104, which is bounded by light transmissive surfaces composed of glass, quartz, plastics, positioned to allow passage of a light beam directed along a light path 88 therethrough. The sample holding portion additionally has an internal opening that connects with the interior passage 108 of the sampling tip 106 to allow passage of a fluid therebetween, and another opening 112 to allow introduction of a negative pressure or partial vacuum condition into cavity 104 and thus also to interior passage 108 of the sampling tip. As a preferred construction, sampling tip 106 and sample holding portion 110 will comprise a continuous internal passage of a tubular element, which for miniaturization purposes will comprise a thin tubular capillary having a desired sectional extent in at least one dimension, e.g., 1 mm outside dimension and 0.7 mm inside dimension, although it is understood that larger sizes can be used.

Thus in operation it is understood that by the introduction of a negative pressure or partial vacuum condition into sampling portion 110 and thus communicated into sampling tip 106 a sample quantity of an analyte of liquid, vapor, or gaseous composition can be drawn via sampling tip 106 into cavity 104 of sample holding portion 110 and retained by the negative pressure condition during analysis. It is also understood that the sample analyte can be ejected by introduction of a positive pressure, and that the internal cavities can be purged prior to receiving a sample.

Figure 27:
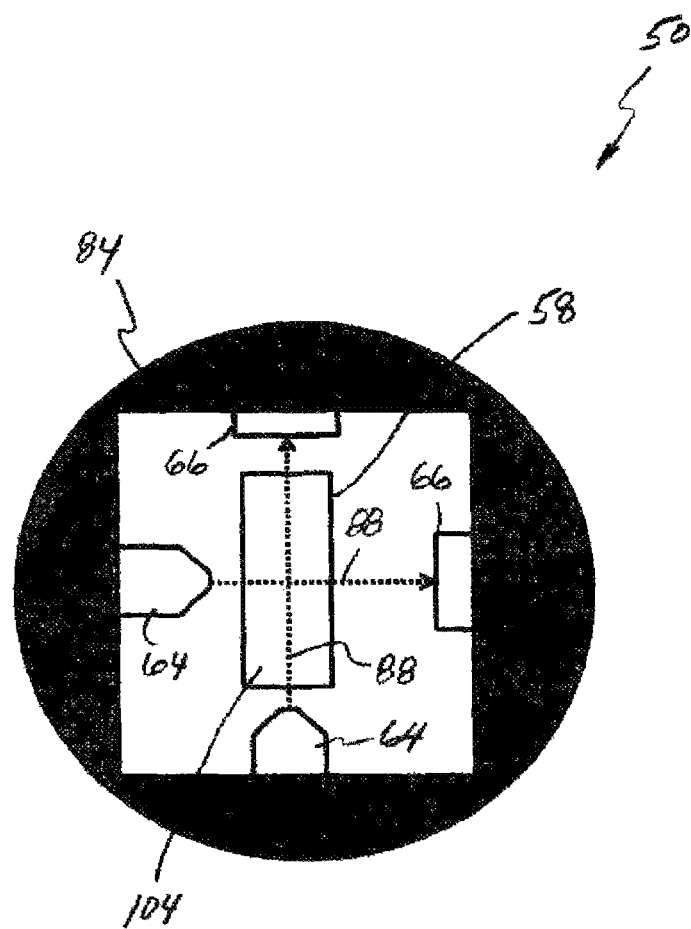
FIG. 27 is an end view of a barrel of a spectrometer of the invention, with a rectangular sample holder, illustrating an alternative light source/detector combination of the invention.
Figure 33:
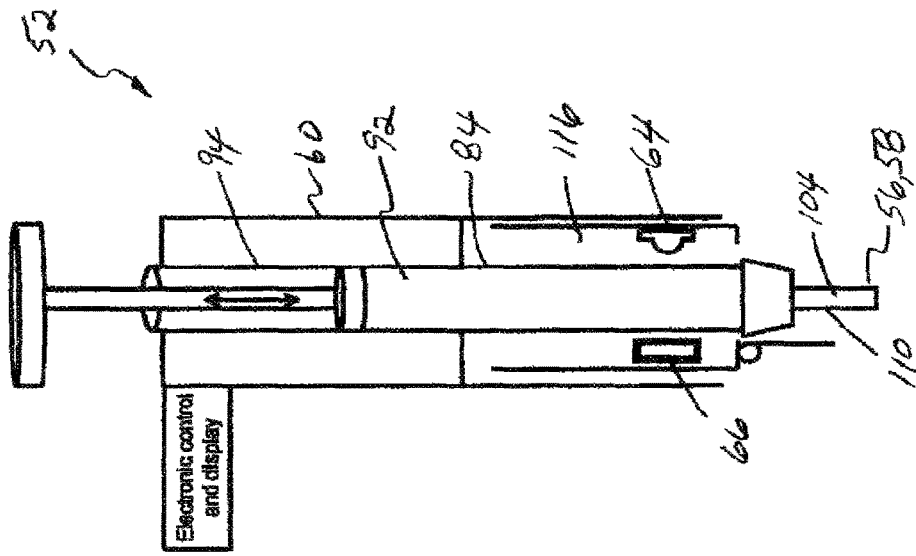
FIG. 33 is another simplified side view of the spectrometer, including the barrel in a retracted position about the sample holder.
Figure 32:
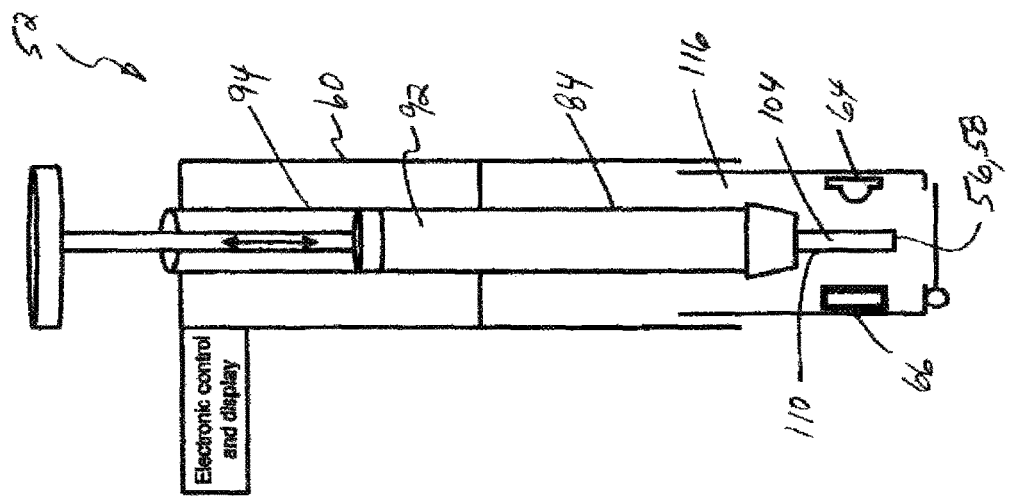
FIG. 32 is a simplified side view of another embodiment of a miniaturized spectrometer of the invention, including a retractable barrel in an extended position about a sample holder.
Figure 35:
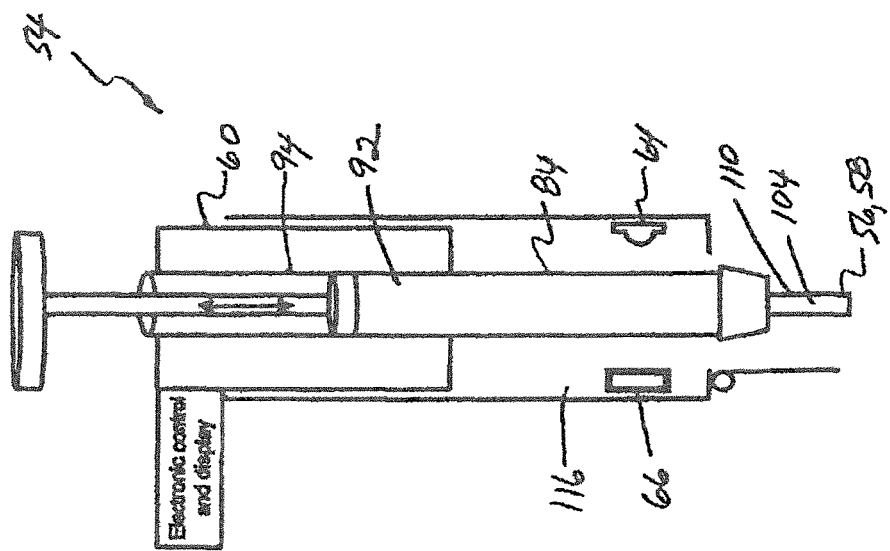
FIG. 35 is another simplified side view of the spectrometer of FIG. 34, including the barrel in a retracted position about the sample holder.
Figure 34:
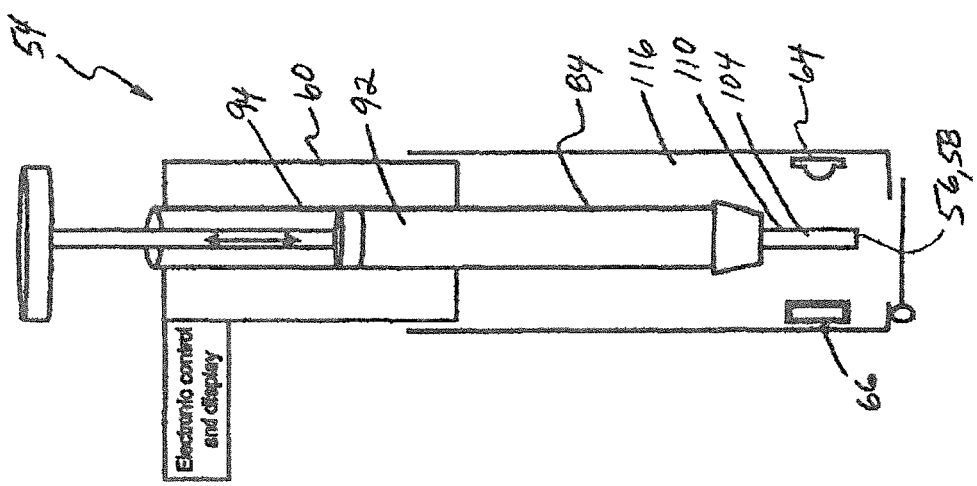
FIG. 34 is a simplified side view of another embodiment of a miniaturized spectrometer of the invention, including a retractable barrel in an extended position about a sample holder.

The light detector or detectors 66 can be disposed directly in the light path 88 of a light source or sources, or beside the light path, e.g., for detecting light scatter or luminescence. In FIG. 27, an arrangement is shown for performing slope spectroscopy, wherein light sources 64 and associated receiving light detectors 66 are angularly related, for passage along different pathlengths through a sample, which will result in a different light absorption values. This can then be used to plot or calculate a slope of light absorption verses distance. It also enables eliminating the need for calibrating to test sample.

To facilitate alignment for the above and other purposes, mounting structure 96 and mounting element 98 can have mating alignment elements 114 such as a detent receivable in a groove or notch, as illustrated in FIGS. 28-31, a visual index, or the like.

As illustrated in FIGS. 32-35, the miniature spectrometers 52 and 54 of the invention are shown providing a retractable enclosure 84 or barrel, so as to be protected within a cavity 116 which can also serve as a light barrier during analysis.

In this embodiment, the sampling tip of the sample holder 56, 58 can be utilized as the sample holding portion 110 and cavity 104.

EXAMPLES

Certain embodiments of the invention will be described in more detail through the following examples. The examples are intended solely to aid in more fully describing selected embodiments of the invention, and should not be considered to limit the scope of the invention in any way.

Example 1

Measurement of Nucleic Acid Concentration and Purity

Figure 4:
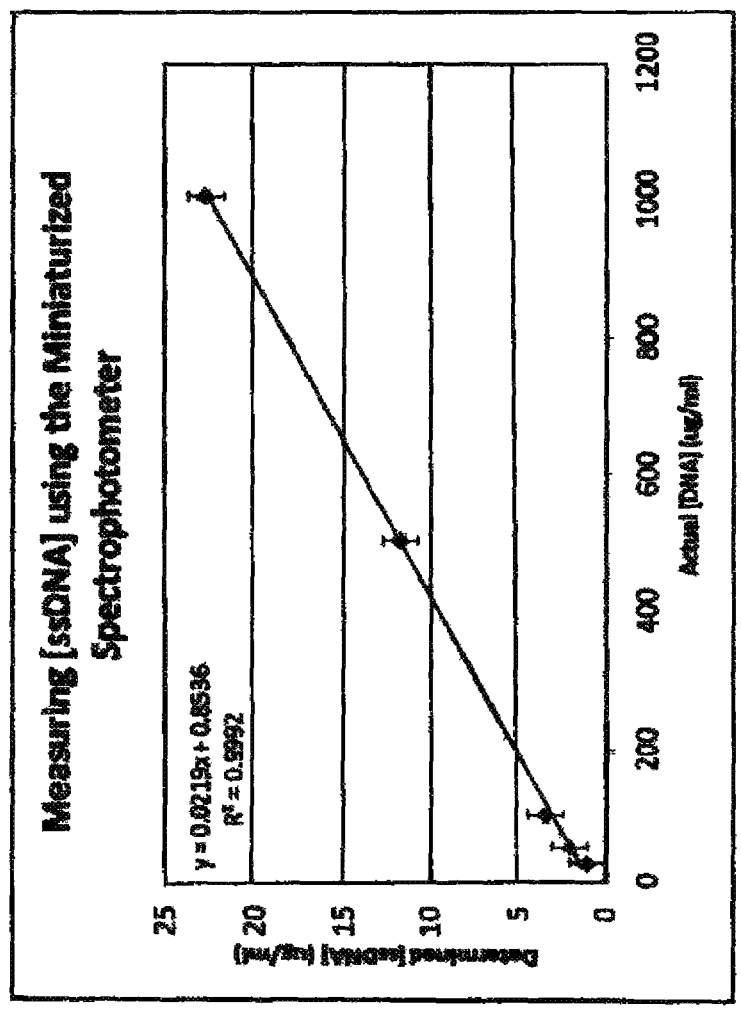
FIG. 4 is a data plot from measuring the concentration of single stranded DNA (ssDNA) using a miniaturized spectrophotometer of the invention to demonstrate sensitivity above 1000 micrograms/milliliter. Measurements were taken using a round 0.7 mm inner diameter quartz capillary, 260 nm led, a broad spectrum photodiode and a voltmeter. Mathematical corrections for differences in light path length but not optical cross section have been applied.

This example uses a miniaturized spectrometer 50, 52, or 54 of the invention to characterize the purity and concentration of extracted nucleic acids in solution. This spectrometer 50, 52, 54 will comprise the basic components of a microprocessor 62 connected to a power source ; three light sources, e.g., light emitting diodes; and three separate light detectors, e.g., photodiodes paired in parallel to permit the measurement of light absorbance by a sample at 230 nm, 260 nm, and 280 nm. Representative apparatus is illustrated in FIGS. 17, 20, and 23. Small sample volumes can be drawn into a capillary tube of defined inner diameter and inserted into the sample holding area of the spectrophotometer. Light absorbance for the given sample can be determined by comparison against a blank sample of solvent. An analog electrical signal from the light detectors(s) 66 is then converted by the microprocessor 62 into digital values representing the intensity of light transmitted through the material. Beer Lambert law allows us to determine absorbance with the equation $[-\log_{10}(p/p^o)]$ where p is the transmitted light for the sample and $p^o$ is the transmitted light for the blank sample. Using the known extinction coefficient for double stranded deoxyribonucleic acid (dsDNA) it is then possible to convert the absorbance values into a concentration. The coextinction value for dsDNA is $(0.02 \ \mu g/ml)^{-1}$ $cm^{-1}$ (Grimsley & Pace, 2003; Powerwave, 2006; Sambrook & Russell, 2001) One absorbance unit for a 1 cm cuvette then is equivalent to 50 µg/ml dsDNA. Using the other two LEDs it is possible to compare the ratio of absorbance at 260-280 nm to determine the degree of contamination by protein. Similarly guanidinium and phenol contamination can be determined by comparing ratios of 260:230 nm. Ideal ratios for 260:280 nm is between 1.8 and 2 AU (absorbance units). Ideal ratios for 260:230 nm are above 1.8 AU. Samples with ratios below this value need to be reprocessed to remove aromatic contaminants. Mathematical corrections for circular cross-sections (vs. square) and decreased light pathlength/diameter (2 mm or less) will be handled by the microprocessor. Data collected through this device will be displayed on an external LCD screen and recorded in a laboratory notebook, or can be wirelessly transmitted to an external device for further analysis and electronic storage. See FIG. 1 which illustrates a typical output display. There are several advantages to this mobile platform. The first is portability. It may be easily transported into different areas in a lab including biological safety hoods, anaerobic glove boxes, personal work benches, clean rooms, common areas etc. This improves laboratory efficiency as it reduces travel between locations where samples are prepared and other locations where it would be measured. A second advantage is expense. This instrument can be manufactured at reduced costs in comparison with standard spectrophotometers and even comparable special use spectrophotometers. Additionally, the use of an LED light source has advantages over incandescent light sources by way of increased energy efficiency and a much greater lifetime. This makes the instrument more available for underfunded labs. Another significant advantage is the increased dynamic range. As illustrated in FIG. 4 this instrument has a dynamic range far greater than standard spectrophotometers using a 1 cm cuvette. Standard spectrometers using 1 cm pathlengths are limited to optical densities of 2 or less. With nucleic acid measurements, this equates to roughly 100 g/ml. This instrument can accurately measure DNA beyond 1 mg/ml. This reduces the need for dilution of sample, thus reducing a common source for error.

Example 2

Measurement of Microbial Cell Density at 600 nm.

Cell culture is a common practice in laboratory settings. It is also common to need to know the density of cells in that culture at a given time or over time to identify the ideal time to sample, harvest, or initiate a process. The most common way to determine cell density is through measuring optical density at a wavelength appropriate for that organism. For *Escherichia coli*, a common organism for biotechnological manipulation, the optimal wavelength for estimating cell density is 600 nm.(Sezonov, Joseleau-Petit, & D'Ari, 2007) A specialized spectrophotometer of the invention is used using the same set up as before except changing to the use of one LED emitting light maximally at 600 nm and one photodiode absorbing light at 600 nm. Such an instrument could be sanitized and utilized within a biological safety hood, thus eliminating the need to take samples to a spectrophotometer. The same instrument could be attached to a bypass stream as part of a bioreactor to measure and even control cellular optical density. This device may be designed for common uses for example absorbance at 600 nm, but it may also be customized according to the customer's needs. For example measuring cell density at 600 nm is not appropriate for cyanobacterial culture where chlorophyll and other pigments mask the cellular component to optical density. In this case an instrument measuring at 750 nm would be more appropriate and thus would use an alternative light source, e.g., an LED emitting at the required wavelength. (Scharnagl, Richter, & Hagemann, 1998) Accordingly, measurement of *Rhodobacter* species is measured at 660 nm due to absorbance of its photosynthetic pigments. (Shah, Perehinec, Stevens, Aizawa, & Sockett, 2000) *Bacillus* species cell culture density however is measured at 470 nm (Santos & Martins, 2003), requiring use of a light source emitting at that wavelength.

Example 3

Colorimetric Assays

Figure 5:
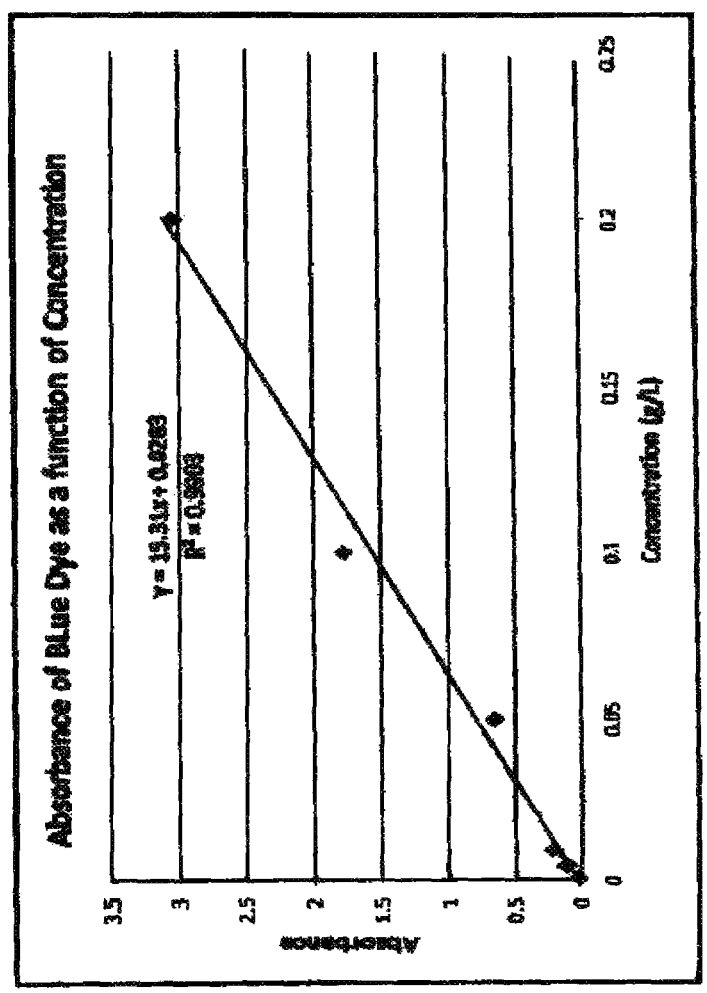
FIG. 5 is a data plot showing absorbance of blue dye as a function of concentration obtained utilizing the miniaturized spectrophotometer of the invention.

A variety of synthesis and purification steps in chemistry and biochemistry utilize colorimetric assays to determine productivity, rate of synthesis, efficiency, and completion. Elisa assays utilize enzyme coupled antibodies to determine the concentration of specific antigens in a given sample. A spectrometer 50, 52, or 54 of the invention can be used to assay the optical properties of solution at the necessary wavelength for the color generated or consumed during the assay. Elisa protocols use a variety of colors for their assays.(Kennedy et al., 1990; Lequin, 2005; Mason, 1993) To accommodate for this, the spectrometer 50, 52, 54, will preferably incorporate several light sources-LEDs configured such that they each illuminate a portion of a fiberoptic cable one at a time. The fiberoptic cable then delivers the appropriate light to the sample. The light sensor could be a broad spectrum photodiode thus enabling detection of any one of the LEDs depending on which is being utilized in the assay. As these assays are generally setup in multi-well plates, it may also be necessary to have this device capable of sampling more than one well at a time. This can be achieved by creating a device with 8, 12, or more channels for analysis at a given time. FIG. 5 shows a representative output of absorbance of a blue dye as a function of concentration that can be generated using a spectrometer of the invention.

Example 4

Luminescence

Luciferase assays are available for a wide range of biotechnological applications. In the presence of luciferase enzyme, D-luciferin reacts with oxygen and ATP and is converted to oxyluciferin, inorganic pyrophosphate, and emits light at high efficiency. Depending on the lucerase enzyme utilized the assay can produce a constant glow, or a quick flash of light. Assays developed by Perkin Elmer are sensitive across 5 orders of magnitude, and sensitive down to 1 fg (Alam & Cook, 1990). These assays are of broad utility for gene expression analysis across multiple species. There are a variety of luciferase enzymes available, most of which emit light in the wavelengths between 550 nm to 620 nm (Close et al., 2012; Gahan, 2012; Meighen, 1993). A miniaturized spectrometer of the invention designed to utilize a photodetector with a spectral absorbance covering this range and a light tight seal around the sampling capillary would be capable of measuring whole (or lysed) cell emission of light from a luciferase assay. These measurements could be utilized to measure gene promoter activity, or as a mechanism to monitor bioreactor productivity when attached to an inline analyzer.

Example 5

Fluorescence

Measuring Fluorescence via a spectrofluorimeter to measure the luminescence of Quinine which is commonly used in fluorescence spectroscopy. Wherein the spectra of quinine is measured by recording the excitation and emission of quinine. This can be used to determine the concentration of quinine in tonic water.

Fluorescence Spectroscopy analysis is used in many applications. Biochemical, chemical, pharmaceutical and medical applications. Also it is used in mineralogy, fluorescent labeling, sensors, and forensic applications. Fluorescence spectroscopy measures the vibrational changes in a sample. Fluorescence spectroscopy can detect proteins, organic compounds, oils, dyes, anthrax, fluorescence in coral, fruit and other flora. Generally Stock solutions are made containing different concentrations of quinine sulfate in methyl and sulfuric acid. The light source of the spectrometer of the invention is directed through a fiber-optic cable set at a 90 degree angle from the detector, to measure the light being emitted rather than detecting the light being transmitted from the source. The light source is warmed up for a period of 15 minutes then a new data point between samples of a blank is taken to help measure drift and minimize error. Peak was recorded at 450 nm max fluorescence for quinine sulfate. Concentrations of 20% to 100% share the same spectral peak of 457.84 nm. The most accurate concentrations of the solute were found in the range of 1 microgram/mL or 1 ppm or 1000 ppb.

DEFINITIONS

Unless otherwise defined, all technical and scientific terms used herein have the same meaning as commonly understood by one of ordinary skill in the art to which this invention pertains. Although methods and materials similar or equivalent to those described herein can be used in the practice or testing of the exemplary embodiments, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

"Handheld device" with the current innovation cycle it is hard to predict what the power and nomenclature of new and developing electronic devices will be in the near future. For that reason the definition for handheld device used in this specification refers broadly to what can be done with the device and its impact on the instant invention rather than current terminology. As used herein, handheld device refers to any equipment that is small enough to be held in the hand that has the ability to receive signals and process those signals to useful output for measurement by the current invention.

In light of all the foregoing, it should thus be apparent to those skilled in the art that there has been shown and described several embodiments of a miniature spectrometer having sensitivity and robustness sufficient for laboratory and field use. However, it should also be apparent that, within the principles and scope of the invention, many changes are possible and contemplated, including in the details, materials, and arrangements of parts which have been described and illustrated to explain the nature of the invention. Thus, while the foregoing description and discussion addresses certain preferred embodiments or elements of the invention, it should further be understood that concepts of the invention, as based upon the foregoing description and discussion, may be readily incorporated into or employed in other embodiments and constructions without departing from the scope of the invention. Accordingly, the following claims are intended to protect the invention broadly as well as in the specific form shown, and all changes, modifications, variations, and other uses and applications which do not depart from the spirit and scope of the invention are deemed to be covered by the invention, which is limited only by the claims which follow.

What is claimed is:
1. A miniaturized spectrometer, comprising:
   a body comprising:
      an enclosure having a sufficiently small size and mass to be carried by a hand from place to place and defining an internal cavity with an opening connected thereto;
      a mounting structure disposed about or adjacent to the opening;

at least one light source disposed and operable to emit a light beam along a light path within the internal cavity in predetermined relation to the mounting structure;

at least one light detector disposed along the light path to receive the light beam, or to receive a portion of the light beam reflected by an object in the light path, or to receive a light emission from the object, and to output at least one signal representative thereof;

a partial vacuum producing apparatus in fluid communication with the internal cavity of the enclosure; and a processor connected to the light detector for receiving the signal outputted thereby, programmed to automatically process the at least one signal to determine at least one characteristic of an object in the light path;

a tubular sample holder comprising:

a mounting element releasably held in the mounting structure via an at least substantially sealed connection, the tubular sample holder extending outwardly from the mounting structure; and a tubular extension extending from the mounting element through the opening of the enclosure and into the internal cavity, the tubular extension comprising an open end of the sample holder and having a light transmissive hollow portion disposed in the light path;

wherein the partial vacuum producing apparatus produces a partial vacuum condition in the tubular extension to draw any liquid within the sample holder into the light transmissive hollow portion of the tubular extension but not to the open end of the sample holder.

2. The miniaturized spectrometer of claim 1, wherein the mounting element comprises a light blocking material that will substantially block transmission of light through the opening of the enclosure.

3. The miniaturized spectrometer of claim 1, wherein at least the hollow light transmissive portion of the tubular extension has an internal sectional extent of less than about 12 mm.

4. The miniaturized spectrometer of claim 1, wherein at least the hollow light transmissive portion of the tubular extension has a round or oval cross sectional shape.

5. The miniaturized spectrometer of claim 1, wherein at least the hollow light transmissive portion of the tubular extension has a scalene triangular cross sectional shape.

6. The miniaturized spectrometer of claim 5, wherein the at least one light source comprises at least two light sources positioned to emit light beams along angularly related light paths.

7. The miniaturized spectrometer of claim 6, wherein the mounting structure and the mounting element are positioned to align sides of the hollow light transmissive portion at predetermined angles to the angularly related light paths.

8. The miniaturized spectrometer of claim 1, wherein the tubular extension has a rectangular cross sectional shape.

9. The miniaturized spectrometer of claim 8, wherein the at least one light source comprises at least two light sources positioned to emit light beams along angularly related light paths.

10. The miniaturized spectrometer of claim 9, wherein the mounting structure and the mounting element are positioned to align sides of the hollow light transmissive portion at predetermined angles to the angularly related light paths.

11. The miniaturized spectrometer of claim 1, wherein the tubular sample holder comprises a hollow tubular capillary.

12. The miniaturized spectrometer of claim 1, wherein the mounting structure and the mounting element have mating polygonal shape features.

13. The miniaturized spectrometer of claim 1, wherein the body further comprises: an input device connected to the processor and operable to input operating commands thereto.

14. The miniaturized spectrometer of claim 1, wherein the body further comprises: a display device connected to the processor and operable to display at least information representative of the at least one characteristic.

15. The miniaturized spectrometer of claim 1, wherein the body further comprises: an output device connected to the processor and operable to output at least information representative of the at least one characteristic.

16. The miniaturized spectrometer of claim 1, wherein the body further comprises: a power source connected to the processor, the light source, and the light detector to provide power thereto.

17. The miniaturized spectrometer of claim 1, wherein the body further comprises: a memory device connected to the processor.

18. The miniaturized spectrometer of claim 1, wherein the at least one characteristic comprises a light absorption value.

19. The miniaturized spectrometer of claim 1, wherein the at least one characteristic comprises a light scattering value.

20. The miniaturized spectrometer of claim 1, wherein the at least one characteristic comprises a fluorescence value.

21. The miniaturized spectrometer of claim 1, wherein the at least one light source comprises a first light source operable to emit a first light beam having a wavelength of about 260 nm, and a second light source operable to emit a second light beam having a wavelength of about 280 nm.

22. The miniaturized spectrometer of claim 21, wherein the first light source is disposed to emit the first light beam along a first light path, and the second light source is disposed to emit the second light beam emitted along a second light path different from the first light path.

23. The miniaturized spectrometer of claim 21, wherein the at least one light source additionally comprises a third light source operable to emit a third light beam having a wavelength of about 230 nm along a light path different from the first and second light paths.

24. The miniaturized spectrometer of claim 1, wherein the at least one light detector comprises a first light detector operable to receive only light having a wavelength of about 260 nm, and a second light detector operable to receive only light having a wavelength of about 280 nm.

25. The miniaturized spectrometer of claim 24, wherein the at least one light detector comprises a third light detector operable to receive only light having a wavelength of about 230 nm.

26. The miniaturized spectrometer of claim 1, wherein the at least one light detector comprises a light detector disposed beside the light path to receive a luminescence emission from an object disposed in the light path.

27. The miniaturized spectrometer of claim 1, wherein the at least one light detector comprises a light detector disposed beside the light path to receive scattered light emissions from an object disposed in the light path.

28. The miniaturized spectrometer of claim 1, wherein the at least one light detector is operable to output a voltage signal representative of a received light emission, and the processor is programmed to determine a light scattering value as a function of the outputted signal.

29. The miniaturized spectrometer of claim 1, wherein the at least one light detector is operable to output a voltage signal representative of a received light emission, and the processor is programmed to determine a fluorescence value as a function of the outputted signal.

30. The miniaturized spectrometer of claim 1, wherein the at least one light detector is operable to output a voltage signal representative of a received light emission, and the processor is programmed to determine a light absorption value as a function of the outputted signal.

* * * * *